(12) United States Patent
Sakamoto

(10) Patent No.: US 11,120,543 B2
(45) Date of Patent: Sep. 14, 2021

(54) MEASUREMENT PROCESSING DEVICE

(71) Applicant: OLYMPUS CORPORATION, Tokyo (JP)

(72) Inventor: Yohei Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 86 days.

(21) Appl. No.: 16/280,128

(22) Filed: Feb. 20, 2019

(65) Prior Publication Data

US 2019/0188842 A1 Jun. 20, 2019

Related U.S. Application Data

(63) Continuation of application No. PCT/JP2017/026133, filed on Jul. 19, 2017.

(30) Foreign Application Priority Data

Aug. 26, 2016 (JP) .............................. JP2016-165562

(51) Int. Cl.
*G06K 9/00* (2006.01)
*G06T 7/00* (2017.01)
*A61B 1/00* (2006.01)
*G06T 7/593* (2017.01)
(Continued)

(52) U.S. Cl.
CPC ............ *G06T 7/001* (2013.01); *A61B 1/0005* (2013.01); *A61B 1/00009* (2013.01);
(Continued)

(58) Field of Classification Search
CPC ............ A61B 1/00009; A61B 1/00093; A61B 1/0005; A61B 1/00057; A61B 1/00193;
(Continued)

(56) References Cited

U.S. PATENT DOCUMENTS

2007/0165306 A1* 7/2007 Bendall .................... A61B 1/05
                                                                        359/464
2008/0027277 A1* 1/2008 Nakano ................ A61B 5/1079
                                                                        600/109
(Continued)

FOREIGN PATENT DOCUMENTS

JP       2011-145527 A       7/2011
JP       2011-170276 A       9/2011
(Continued)

OTHER PUBLICATIONS

International Search Report dated Oct. 3, 2017 issued in PCT/JP2017/026133.

*Primary Examiner* — Sean M Conner
(74) *Attorney, Agent, or Firm* — Scully, Scott, Murphy & Presser, P.C.

(57) ABSTRACT

A measurement processing device includes an imaging unit, an image acquisition unit, a display unit, a measurement point display control unit, a corresponding-point calculation unit, a corresponding-point image generation unit, and a corresponding-point image display control unit. The measurement point display control unit causes a measurement point indicating a measurement position designated by a user to be displayed on a first image. The corresponding-point image generation unit generates a corresponding-point image that includes the corresponding point calculated by the corresponding-point calculation unit and a region in the vicinity of the corresponding point in the second image and is constituted of all or a part of the second image. The corresponding-point image display control unit causes the corresponding-point image to be displayed so that a straight line passing through the measurement point and the corresponding point is orthogonal to the parallax direction on a display screen.

18 Claims, 27 Drawing Sheets

(51) Int. Cl.
*G02B 23/24* (2006.01)
*G01B 11/25* (2006.01)
*G06T 7/55* (2017.01)
*G06T 7/62* (2017.01)
*G01B 11/02* (2006.01)
*H04N 5/225* (2006.01)

(52) U.S. Cl.
CPC ...... *A61B 1/00039* (2013.01); *A61B 1/00057* (2013.01); *A61B 1/00193* (2013.01); *G01B 11/022* (2013.01); *G01B 11/2545* (2013.01); *G02B 23/2415* (2013.01); *G06T 7/00* (2013.01); *G06T 7/55* (2017.01); *G06T 7/593* (2017.01); *G06T 7/62* (2017.01); *H04N 5/2256* (2013.01); *H04N 2005/2255* (2013.01)

(58) Field of Classification Search
CPC .............. G01B 11/022; G01B 11/2545; G02B 23/2415; G06T 7/00; G06T 7/001; G06T 7/55; G06T 7/593; G06T 7/62; H04N 2005/2255; H04N 5/2256

See application file for complete search history.

(56) References Cited

U.S. PATENT DOCUMENTS

| | | |
|---|---|---|
| 2011/0178371 A1 | 7/2011 | Nakano |
| 2018/0357783 A1* | 12/2018 | Takahashi .......... G06K 9/00805 |
| 2019/0230334 A1* | 7/2019 | Kano ..................... H04N 5/232 |
| 2019/0279381 A1* | 9/2019 | Hasegawa ............. G06T 11/001 |

FOREIGN PATENT DOCUMENTS

| | | |
|---|---|---|
| JP | 2014-026217 A | 2/2014 |
| JP | 2016-095458 A | 5/2016 |
| JP | 2016-121917 A | 7/2016 |

* cited by examiner

MEASUREMENT PROCESSING DEVICE

The present application claims priority to Japanese Patent Application No. 2016-165562, filed on Aug. 26, 2016 and is a continuation application based on PCT Patent Application No. PCT/JP2017/026133, filed on Jul. 19, 2017, and the contents of both the Japanese patent application and the PCT patent application are incorporated herein by reference.

BACKGROUND OF THE INVENTION

Field of the Invention

The present invention relates to a measurement processing device.

Description of Related Art

Industrial endoscope devices are used for observation and inspection for internal scratches and corrosion in boilers, turbines, engines, pipes, and the like. In these endoscope devices, a plurality of types of optical adapters for observing and inspecting various observation subjects are provided and distal end portions of endoscopes can be replaced. As one of such endoscope devices, there is an endoscope device for three-dimensional measurement that implements three-dimensional measurement using a stereo-optical system having two optical systems with different parallaxes. This endoscope device for three-dimensional measurement has a function of measuring a length, an area, and the like on the basis of measurement points designated on a captured image.

In an endoscope device for three-dimensional measurement, it is necessary to accurately and precisely measure a length and an area of a scratch (a defect) of an object. In the three-dimensional measurement using a stereo-optical system, a matching process is performed to search for a point (a corresponding point) which is a position corresponding to that of a measurement point designated by the user on one of left and right images in the other of the left and right images. However, there is a possibility that the measurement performance will deteriorate due to erroneous matching correspondence according to the imaging conditions such as a positional relationship (an object distance and an angle) between the object and the endoscope, the brightness of illumination, and a shape and properties of the object. Erroneous matching correspondence is a phenomenon that a point different from a true corresponding point is recognized as a corresponding point when a matching process is performed. For example, a phenomenon that the illumination light of the endoscope is regularly reflected on a surface of an object and the reflected light appears in the observation image, i.e., halation, may occur. When measurement is performed in a region where light due to regular reflection of the illumination light appears, erroneous matching correspondence is likely to occur. The measurement performance deteriorates due to the occurrence of erroneous matching correspondence. Thus, a user is required to pre-check whether or not erroneous matching correspondence will occur with respect to a designated measurement point.

Technology for enabling a user to more easily check whether or not erroneous matching correspondence has occurred has been disclosed. For example, in Japanese Unexamined Patent Application, First Publication No. 2011-170276, technology in which a part of a left image including a measurement point designated by a user and a part of a right image including a corresponding point obtained in a matching process are arranged on left and right sides and displayed on a monitor is disclosed.

SUMMARY OF THE INVENTION

According to a first aspect of the present invention, a measurement processing device includes an imaging unit, an image acquisition unit, a display unit, a measurement point display control unit, a corresponding-point calculation unit, a corresponding-point image generation unit, and a corresponding-point image display control unit. The imaging unit images an object and generates an imaging signal. The image acquisition unit acquires a first image and a second image mutually having parallax in a predetermined parallax direction on the basis of the imaging signal. The display unit has a display screen on which the first image is displayed. The measurement point display control unit causes a measurement point indicating a measurement position designated by a user to be displayed on the first image. The corresponding-point calculation unit calculates a corresponding point on the second image corresponding to the measurement point on the first image. The corresponding-point image generation unit generates a corresponding-point image that includes the corresponding point and a region in the vicinity of the corresponding point in the second image and is constituted of all or a part of the second image. The corresponding-point image display control unit causes the corresponding-point image to be displayed on the display screen. The corresponding-point image display control unit causes the corresponding-point image to be displayed on the display screen so that a straight line passing through the measurement point and the corresponding point is orthogonal to the parallax direction.

According to a second aspect of the present invention, in the first aspect, the corresponding-point image display control unit may cause the corresponding-point image to be displayed so that the corresponding point is separated from the measurement point.

According to a third aspect of the present invention, in the first aspect, the corresponding-point image generation unit may generate the corresponding-point image of which a length in the parallax direction is greater than a length in a direction orthogonal to the parallax direction.

According to a fourth aspect of the present invention, in the third aspect, the corresponding-point image generation unit may generate a second corresponding-point image of which the length in the parallax direction is less than the length in the direction orthogonal to the parallax direction. The second corresponding-point image includes the corresponding point and a region in the vicinity of the corresponding point in the second image and is constituted of all or a part of the second image. The corresponding-point image display control unit may cause the second corresponding-point image to be displayed on the display screen so that the first image and the second corresponding-point image are arranged in the parallax direction.

According to a fifth aspect of the present invention, in the fourth aspect, the measurement processing device may further include an auxiliary line display control unit configured to cause an auxiliary line parallel to the parallax direction and passing through the measurement point to be displayed on the first image and the second corresponding-point image on the display screen.

According to a sixth aspect of the present invention, in the second aspect, the measurement processing device may further include an auxiliary line display control unit configured to cause one or more auxiliary lines orthogonal to the parallax direction to be displayed on the first image and the corresponding-point image on the display screen.

According to a seventh aspect of the present invention, in the sixth aspect, the auxiliary line display control unit may cause the auxiliary line to be displayed so that the auxiliary line passes through the measurement point.

According to an eighth aspect of the present invention, in the sixth aspect, the measurement processing device may further include a feature point calculation unit configured to calculate a first feature point other than the measurement point in the object of the first image. The auxiliary line display control unit may cause the auxiliary line to be displayed so that the auxiliary line passes through the first feature point.

According to a ninth aspect of the present invention, in the sixth aspect, the measurement processing device may further include a feature point calculation unit configured to calculate a second feature point other than the corresponding point in the object of the corresponding-point image. The auxiliary line display control unit may cause the auxiliary line to be displayed so that the auxiliary line passes through the second feature point.

According to a tenth aspect of the present invention, in the second aspect, the measurement processing device may further include a feature point calculation unit, a corresponding-feature-point calculation unit, and an auxiliary line display control unit. The feature point calculation unit may calculate a feature point other than the measurement point in the object of the first image. The corresponding-feature-point calculation unit may calculate a corresponding feature point on the second image corresponding to the feature point on the first image. The auxiliary line display control unit may cause an auxiliary line passing through the feature point and the corresponding feature point to be displayed.

According to an eleventh aspect of the present invention, in the second aspect, the corresponding-point image display control unit may control a display position of the corresponding-point image in accordance with a position of the measurement point.

According to a twelfth aspect of the present invention, in the eleventh aspect, the corresponding-point image display control unit may set a plurality of image regions arranged in a direction orthogonal to the parallax direction in the first image. The plurality of image regions may include a first image region and a second image region. A direction orthogonal to the parallax direction and directed from the first image region to the second image region may be defined as a first direction. A direction orthogonal to the parallax direction and directed from the second image region to the first image region may be defined as a second direction. The corresponding-point image display control unit may cause the corresponding-point image to be displayed at a position on the first direction side of the measurement point when the measurement point is located within the first image region. The corresponding-point image display control unit may cause the corresponding-point image to be displayed at a position on the second direction side of the measurement point when the measurement point is located within the second image region.

According to a thirteenth aspect of the present invention, in the twelfth aspect, the corresponding-point image display control unit may cause the corresponding-point image to be displayed on the first image.

According to a fourteenth aspect of the present invention, in the eleventh aspect, the corresponding-point image display control unit may set a plurality of image regions arranged in a direction orthogonal to the parallax direction in the first image. The plurality of image regions may include a first image region and a second image region. The corresponding-point image display control unit may cause the corresponding-point image to be displayed in the first image region when the measurement point is located within the first image region. The corresponding-point image display control unit may cause the corresponding-point image to be displayed in the second image region when the measurement point is located within the second image region.

According to a fifteenth aspect of the present invention, in the eleventh aspect, the corresponding-point image display control unit may set a first image region and a second image region obtained by bisecting the first image in a direction orthogonal to the parallax direction in the first image. A direction orthogonal to the parallax direction and directed from the first image region to the second image region may be defined as a first direction. A direction orthogonal to the parallax direction and directed from the second image region to the first image region may be defined as a second direction. The corresponding-point image display control unit may set a first display region at a position on the second direction side of the first image region and set a second display region at a position on the first direction side of the second image region on the display screen. The corresponding-point image display control unit may cause the corresponding-point image to be displayed in the first image region when the measurement point is located within the first image region. The corresponding-point image display control unit may cause the corresponding-point image to be displayed in the second image region when the measurement point is located within the second image region.

According to a sixteenth aspect of the present invention, in the first aspect, the measurement processing device may further include a measurement point image generation unit and a measurement point image display control unit. The measurement point image generation unit may generate a measurement point image that includes the measurement point and a region in the vicinity of the measurement point in the first image and is constituted of a part of the first image. The measurement point image display control unit may cause the measurement point image to be displayed on the display screen. The corresponding-point image display control unit may cause the corresponding-point image to be displayed so that a straight line passing through the measurement point in the measurement point image and the corresponding point in the corresponding-point image is orthogonal to the parallax direction on the display screen.

According to a seventeenth aspect of the present invention, in the sixteenth aspect, the measurement point image display control unit may cause the measurement point image to be displayed at display magnification higher than that of the first image.

According to an eighteenth aspect of the present invention, in the seventeenth aspect, the corresponding-point image display control unit may cause the corresponding-point image to be displayed at the same display magnification as that of the measurement point image.

According to a nineteenth aspect of the present invention, in the first aspect, the measurement processing device may further include a corresponding-point display control unit configured to cause the corresponding point to be displayed on the corresponding-point image. The measurement point display control unit may cause a first cursor indicating the measurement point to be displayed on the straight line on the display screen. The corresponding-point display control unit may cause a second cursor indicating the corresponding point to be displayed on the straight line on the display screen.

According to a twentieth aspect of the present invention, in the first aspect, the corresponding-point image display control unit may cause the corresponding-point image to be displayed at the same display magnification as that of the first image.

DETAILED DESCRIPTION OF THE INVENTION

Hereinafter, embodiments of the present invention will be described with reference to the drawings.

First Embodiment

Figure 1:
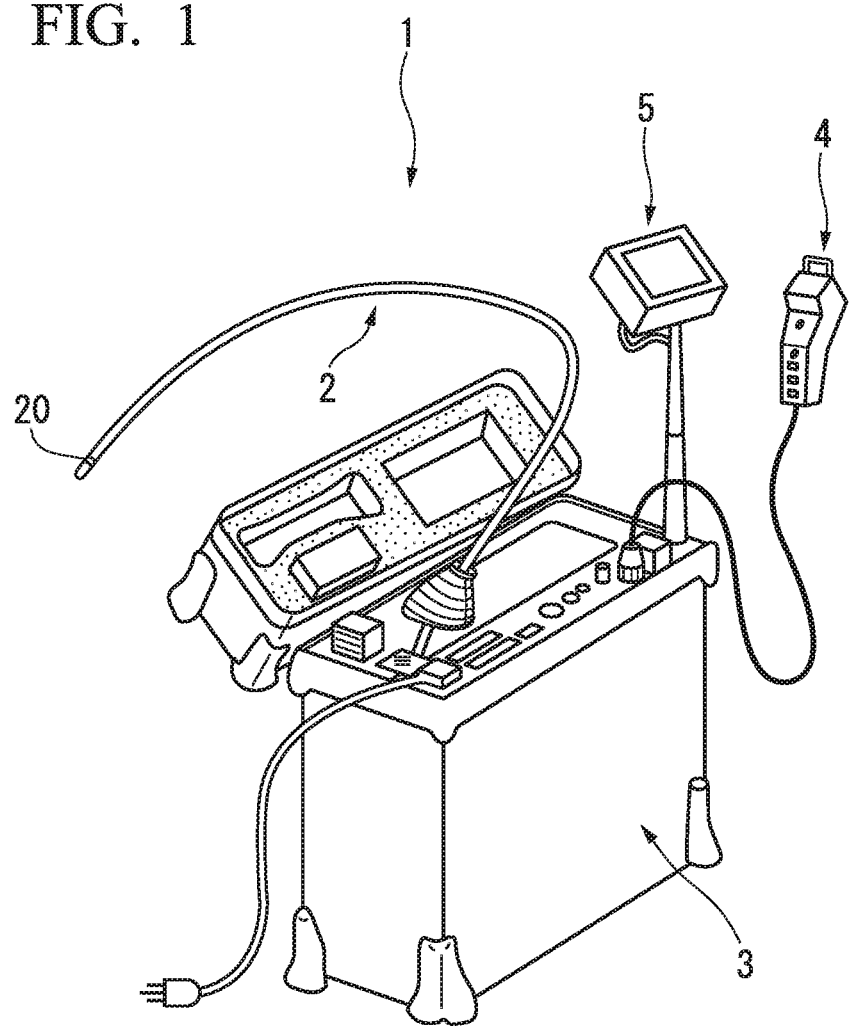
FIG. 1 is a perspective view showing an overall configuration of an endoscopic measurement device according to a first embodiment of the present invention.

FIG. 1 shows an exterior of an endoscopic measurement device 1 (a measurement processing device) according to a first embodiment of the present invention. The endoscopic measurement device 1 images an object and measures a geometric characteristic of the object from an image. To observe and measure various objects, an inspector can perform exchanging an optical adapter attached to a distal end of an insertion unit 2, the selection of a built-in measurement processing program, and the addition of a measurement processing program. Hereinafter, a case in which stereo measurement is performed will be described as an example of measurement.

As shown in FIG. 1, the endoscopic measurement device 1 includes the insertion unit 2, a main body unit 3, an operation unit 4, and a display unit 5 (a monitor).

The insertion unit 2 is inserted into the object. The insertion unit 2 has an elongated tubular shape in which a range from a distal end 20 to a proximal end portion can be bent. The insertion unit 2 images a measurement portion and outputs an imaging signal to the main body unit 3. A stereo-optical adapter 30 (FIGS. 3 and 4) is mounted on the distal end 20 of the insertion unit 2. The main body unit 3 is a control device including a housing portion for housing the insertion unit 2. The operation unit 4 receives a user's operation on the endoscopic measurement device 1. The display unit 5 has a display screen and displays an image of the object imaged by the insertion unit 2, an operation menu, and the like on the display screen.

Figure 2:
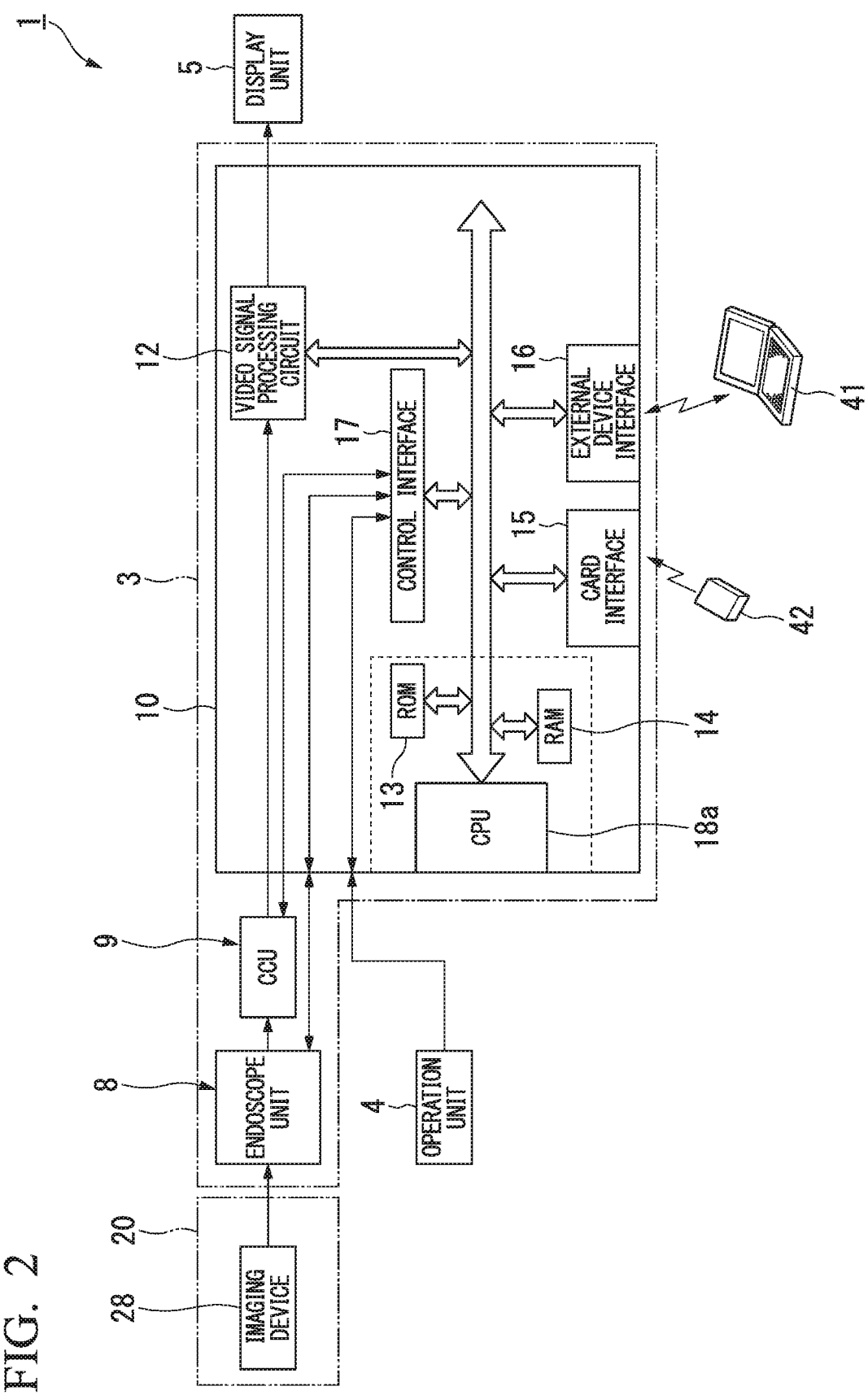
FIG. 2 is a block diagram showing an internal configuration of an endoscopic measurement device according to the first embodiment of the present invention.

As shown in FIG. 2, the main body unit 3 includes an endoscope unit 8, a camera control unit (CCU) 9, and a control device 10. The endoscope unit 8 has a light source device for supplying illumination light necessary for observation and a bending device for causing a bendable portion (not shown) to be bent. An imaging device 28 is built into the distal end 20 of the insertion unit 2. The imaging device 28 photoelectrically converts the object image formed via the stereo-optical adapter 30 and generates an imaging signal. The CCU 9 drives the imaging device 28. The imaging signal output from the imaging device 28 is input to the CCU 9. The CCU 9 performs pre-processing including amplification, noise removal, and the like on the imaging signal acquired by the imaging device 28. The CCU 9 converts the imaging signal on which the pre-processing has been performed into a video signal such as an NTSC signal.

The control device 10 includes a video signal processing circuit 12, a read only memory (ROM) 13, a random access memory (RAM) 14, a card interface 15, an external device interface 16, a control interface 17, and a central processing unit (CPU) 18a.

The video signal processing circuit 12 performs predetermined video processing on the video signal output from the CCU 9. For example, the video signal processing circuit 12 synthesizes the video signal output from the CCU 9 with a graphic image signal generated by the CPU 18a. The graphic image signal includes an image of an operation screen, measurement information, and the like. The measurement information includes an image of a cursor, an image of an auxiliary line, a measurement result, and the like. The video signal processing circuit 12 outputs a synthesized video signal to the display unit 5.

The ROM 13 is a nonvolatile recording medium in which a program for enabling the CPU 18a to control an operation of the endoscopic measurement device 1 is recorded. The RAM 14 is a volatile recording medium that temporarily stores information to be used by the CPU 18a to control the endoscopic measurement device 1. The CPU 18a controls an operation of the endoscopic measurement device 1 on the basis of the program recorded in the ROM 13.

A memory card 42 which is a detachable recording medium is connected to the card interface 15. The card interface 15 inputs control processing information, image information, and the like stored in the memory card 42 to the control device 10. Also, the card interface 15 records control processing information, image information, and the like generated by the endoscopic measurement device 1 in the memory card 42.

An external device such as a USB device is connected to the external device interface 16. For example, a personal computer 41 is connected to the external device interface 16. The external device interface 16 performs transmission of information to the personal computer 41 and reception of information from the personal computer 41. Thereby, the monitor of the personal computer 41 can display information. Also, the user can perform operations related to the control of the endoscopic measurement device 1 via the personal computer 41.

The control interface 17 performs communication for operation control with the operation unit 4, the endoscope unit 8, and the CCU 9. The control interface 17 notifies the CPU 18a of an instruction input by the user via the operation unit 4. The control interface 17 outputs control signals for controlling the light source device and the bending device to the endoscope unit 8. The control interface 17 outputs a control signal for controlling the imaging device 28 to the CCU 9.

The program to be executed by the CPU 18a may be recorded in a computer readable recording medium. The program recorded in the recording medium may be read and executed by a computer other than the endoscopic measurement device 1. For example, the personal computer 41 may read and execute the program. The personal computer 41 may control the endoscopic measurement device 1 by transmitting control information for controlling the endoscopic measurement device 1 to the endoscopic measurement device 1 in accordance with the program. Alternatively, the personal computer 41 may acquire a video signal from the endoscopic measurement device 1 and perform measurement using the acquired video signal.

Also, the above-described program may be transmitted from a computer having a storage device or the like storing the program to the endoscopic measurement device 1 via a transmission medium or by transmission waves in a transmission medium. The "transmission medium" for transmitting the program refers to a medium having a function of transmitting information, like a network (a communication network) such as the Internet or a communication circuit (a communication line) such as a telephone circuit. Also, the above-described program may implement some of the above-described functions. Further, the above-described program may be a differential file (a differential program) capable of implementing the above-described function in combination with a program already recorded on the computer.

Figure 3:
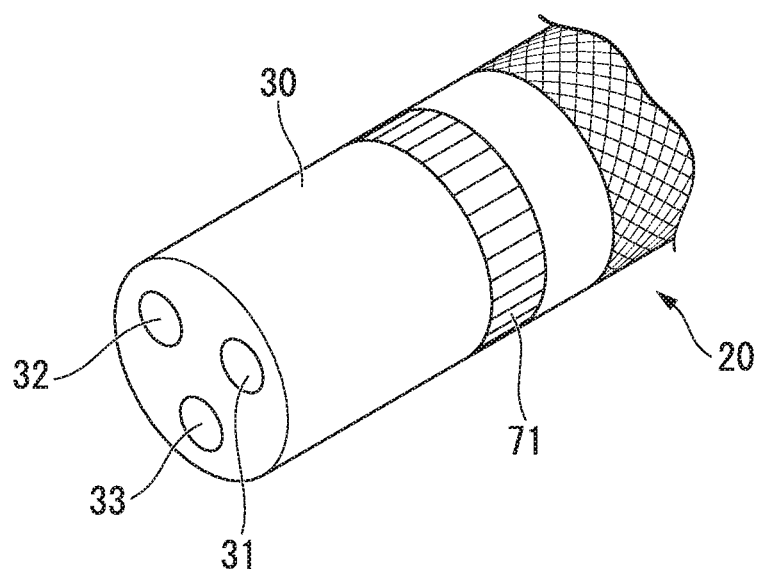
FIG. 3 is a perspective view showing a configuration of a distal end of an insertion unit and a stereo-optical adapter in the endoscopic measurement device according to the first embodiment of the present invention.
Figure 4:
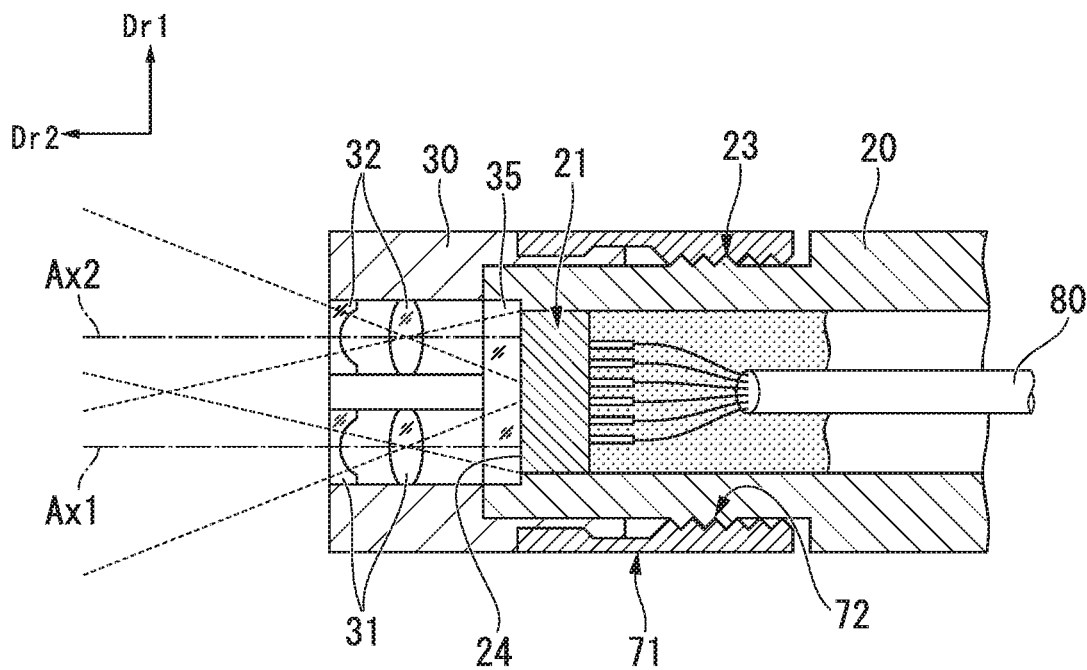
FIG. 4 is a cross-sectional view showing the configuration of the distal end of the insertion unit and the stereo-optical adapter in the endoscopic measurement device according to the first embodiment of the present invention.

FIGS. 3 and 4 show configurations of the distal end 20 of the insertion unit 2 and the stereo-optical adapter 30. FIG. 3 shows an exterior of the distal end 20 of the insertion unit 2 and the stereo-optical adapter 30. FIG. 4 shows a cross section of the distal end 20 of the insertion unit 2 and the stereo-optical adapter 30. In FIG. 4, a cross section including the first optical system 31 and the second optical system 32 is shown.

The stereo-optical adapter 30 is mounted on the distal end 20 of the insertion unit 2. The stereo-optical adapter 30 is screwed and fixed to a male screw 23 of the distal end 20 of the insertion unit 2 by a female screw 72 of a fixing ring 71. A first optical system 31, a second optical system 32, and an illumination window 33 are provided on the distal end of the stereo-optical adapter 30. The first optical system 31 and the second optical system 32 include an objective lens. The first optical system 31 and the second optical system 32 are separated in a parallax direction Dr1. The first optical system 31 is disposed on a left side facing the object and the second optical system 32 is disposed on a right side. An optical axis Ax1 of the first optical system 31 and an optical axis Ax2 of the second optical system 32 are disposed in a direction Dr2 intersecting the parallax direction Dr1. In other words, the optical axis Ax1 of the first optical system 31 and the optical axis Ax2 of the second optical system 32 are disposed to face the direction Dr2. The parallax direction Dr1 is a direction of a straight line passing through a first optical center (a principal point) of the first optical system 31 and a second optical center (a principal point) of the second optical system 32. The direction Dr2 is orthogonal to the parallax direction Dr1. The first optical system 31 and the second optical system 32 form two images of the object on the imaging device 28 provided within the distal end 20 of the insertion unit 2. The first optical system 31 forms a first optical image and the second optical system 32 forms a second optical image.

The first optical image and the second optical image mutually have parallax. A measurement point is designated in the first image corresponding to the first optical image. The first optical system 31 may be disposed on the right side facing the object and the second optical system 32 may be disposed on the left side.

The imaging device 28 is an image sensor. The imaging device 28 is disposed on the distal end 20 of the insertion unit 2. The imaging device 28 has an imaging plane 24 disposed at image formation positions of the first optical system 31 and the second optical system 32. The imaging device 28 generates an imaging signal from a first optical image formed on the imaging plane 24 via the first optical system 31 and a second optical image formed on the imaging plane 24 via the second optical system 32. In other words, the imaging device 28 generates a first image corresponding to the first optical image obtained via the first optical system 31 and a second image corresponding to the second optical image obtained via the second optical system 32. The first image and the second image mutually have parallax. In the first embodiment, an image corresponding to a left visual field is defined as the first image and an image corresponding to a right visual field is defined as the second image. An image corresponding to the right visual field may be defined as the first image and an image corresponding to the left visual field may be defined as the second image.

The imaging device 28 is connected to a signal line 80 and the imaging signal is output from the imaging device 28 to the signal line 80. A cover glass 35 for protecting the imaging device 28 is disposed on an end surface of the distal end 20 of the insertion unit 2.

As described above, the endoscopic measurement device 1 includes the imaging device 28 (an imaging unit), the CCU 9 (an image acquisition unit), the display unit 5, and the CPU 18a. The imaging device 28 images an object and generates an imaging signal. The CCU 9 generates a video signal on the basis of the imaging signal. The video signal includes an image of the object. Therefore, the CCU 9 acquires the first image and the second image mutually having parallax in a predetermined parallax direction on the basis of the imaging signal. The display unit 5 has a display screen on which the first image is displayed.

Figure 5:
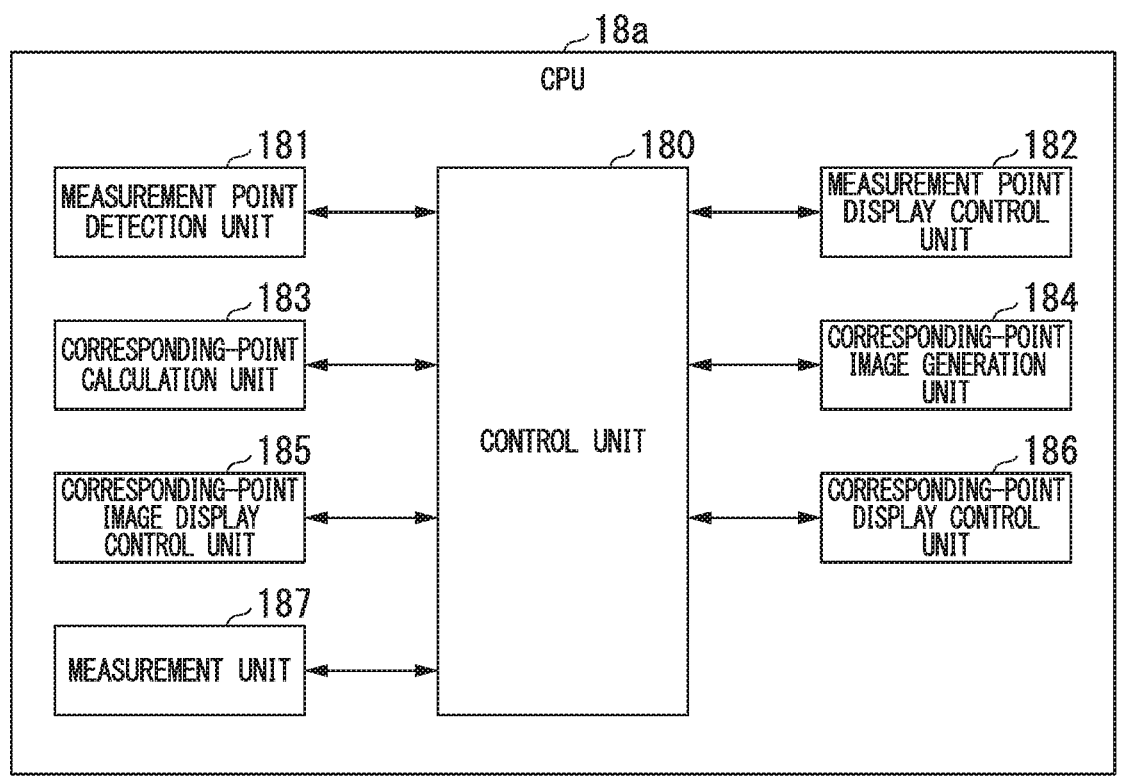
FIG. 5 is a block diagram showing a functional configuration of a CPU according to the first embodiment of the present invention.

FIG. 5 shows a functional configuration of the CPU 18a. A control unit 180, a measurement point detection unit 181, a measurement point display control unit 182, a corresponding-point calculation unit 183, a corresponding-point image generation unit 184, a corresponding-point image display control unit 185, a corresponding-point display control unit 186, and a measurement unit 187 constitute functions of the CPU 18a. At least one of the blocks shown in FIG. 5 may include a circuit different from the CPU 18a.

The control unit 180 controls a process to be performed by each unit. The measurement point detection unit 181 monitors a state of the operation unit 4 operated by the user and detects a measurement point indicating a measurement position designated by the user in the first image. The measurement point display control unit 182 causes the measurement point designated by the user to be displayed on the first image. For example, the measurement point display control unit 182 causes a first cursor that is a mark indicating the measurement point to be displayed at the position of the measurement point on the first image. The corresponding-point calculation unit 183 calculates a corresponding point on the second image corresponding to the measurement point on the first image. Generally, this process is called a matching process.

The corresponding-point image generation unit 184 generates a corresponding-point image that includes the corresponding point calculated by the corresponding-point calculation unit 183 and a region in the vicinity of the corresponding point in the second image and is constituted of all or a part of the second image. The corresponding-point image display control unit 185 causes the corresponding-point image to be displayed on the display screen. At this time, the corresponding-point image display control unit 185 causes the corresponding-point image to be displayed on the display screen so that a straight line passing through the measurement point and the corresponding point is orthogonal to the parallax direction. The corresponding-point display control unit 186 causes the corresponding point to be displayed on the corresponding-point image. For example, the corresponding-point display control unit 186 causes a second cursor that is a mark indicating the corresponding point to be displayed at the position of the corresponding point on the corresponding-point image. The measurement unit 187 calculates three-dimensional coordinates of the measurement point in accordance with the principle of triangulation on the basis of two-dimensional coordinates of the measurement point and the corresponding point. The measurement unit 187 measures a size of the three-dimensional shape of the object on the basis of the three-dimensional coordinates of the measurement point.

When the measurement point display control unit 182 causes the first cursor to be displayed, the measurement point display control unit 182 generates a graphic image signal of the first cursor. The measurement point display control unit 182 outputs the generated graphic image signal to the video signal processing circuit 12. The video signal processing circuit 12 synthesizes the video signal output from the CCU 9 with the graphic image signal output from the CPU 18a. Thereby, the first cursor is superimposed on the first image. The video signal processing circuit 12 outputs the synthesized video signal to the display unit 5. The display unit 5 displays the first image on which the measurement point, i.e., the first cursor, is superimposed.

The corresponding-point image generated by the corresponding-point image generation unit 184 is output to the video signal processing circuit 12. The corresponding-point image display control unit 185 controls a display position of the corresponding-point image so that the position of the corresponding-point image in the first image becomes a desired position. Also, when the corresponding-point image display control unit 185 causes the second cursor to be displayed, the corresponding-point image display control unit 185 generates the graphic image signal of the second cursor. The corresponding-point image display control unit 185 outputs the generated graphic image signal to the video signal processing circuit 12. The video signal processing circuit 12 synthesizes the video signal output from the CCU 9 with the graphic image signal output from the CPU 18a. Thereby, the second cursor is superimposed on the corresponding-point image. The video signal processing circuit 12 outputs the synthesized video signal to the display unit 5. The display unit 5 displays the corresponding-point image on which the corresponding point, i.e., the second cursor, is superimposed.

Figure 6:
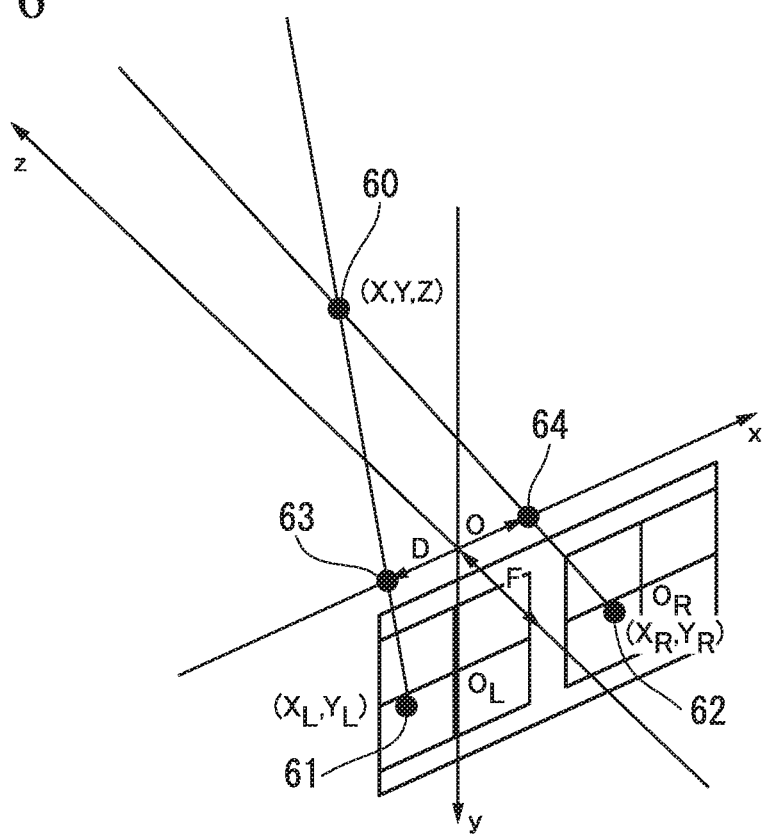
FIG. 6 is a reference diagram showing a method of calculating three-dimensional coordinates of a measurement point in stereo measurement according to the first embodiment of the present invention.

The principle of stereo measurement will be described with reference to FIG. 6. In the stereo measurement, three-dimensional coordinates of an object are calculated using the principle of triangulation on the basis of coordinates of two optical distance measurement points when object images are captured by two optical systems. A middle point of a line segment connecting a left optical center (a first optical center 63) and a right optical center (a second optical center 64) is defined as an origin O. Also, an x-axis whose right direction is positive and a y-axis whose downward direction is positive are defined. Also, a z-axis where a direction away from the optical system in parallel to an optical axis is positive is defined.

Three-dimensional coordinates (X, Y, Z) of a measurement point 60 for an image including object images obtained via the left optical system and the right optical system are calculated by the following Equations (1) to (3) in accordance with the principle of triangulation. However, two-dimensional coordinates of a measurement point 61 on the left image plane subjected to distortion correction and a corresponding point 62 on the right image plane subjected to distortion correction are $(X_L, Y_L)$ and $(X_R, Y_R)$, respectively. Origins of these two-dimensional coordinates are an intersection $O_L$ and an intersection $O_R$ between optical axes of the left optical system and the right optical system and the image planes, respectively. The distance between the first optical center 63 and the second optical center 64 is D. The focal length is F. The parameter t is $D/(X_R-X_L)$.

$$X = t \times X_R + D/2 \quad (1)$$

$$Y = -t \times Y_R \quad (2)$$

$$Z = t \times F \quad (3)$$

When the coordinates of the measurement point 61 and the corresponding point 62 on the image plane are determined as described above, the three-dimensional coordinates of the measurement point 60 can be obtained using the parameter D and the parameter F. By obtaining three-dimensional coordinates of several points, various measurement functions can be implemented. For example, a distance between two points, a distance between a line connecting two points and one point, an area of a region surrounded by a line connecting a plurality of points, a depth of a reference surface, a surface shape, and the like are measured. The user can select a desired measurement function from various measurement functions. It is also possible to obtain a distance (an object distance) from the first optical center 63 or the second optical center 64 to the object. To perform the stereo measurement described above, optical data indicating the characteristics of the optical system including the distal end 20 of the insertion unit 2 and the stereo-optical adapter 30 is required. For example, details of the matching process and the optical data are described in Japanese Unexamined Patent Application, First Publication No. 2004-49638 and therefore a description thereof will be omitted.

Figure 7:
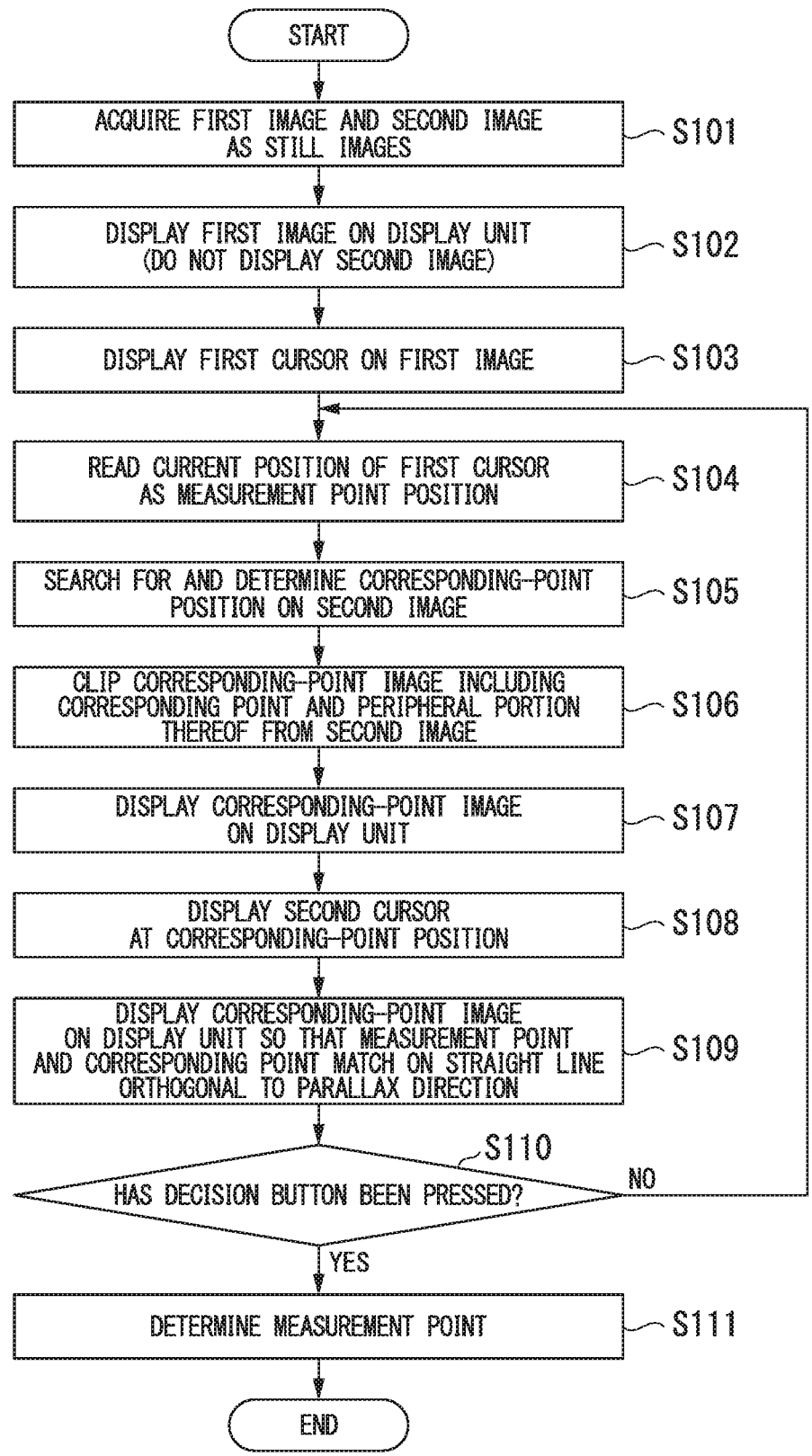
FIG. 7 is a flowchart showing a procedure of an operation of the endoscopic measurement device according to the first embodiment of the present invention.
Figure 8A:
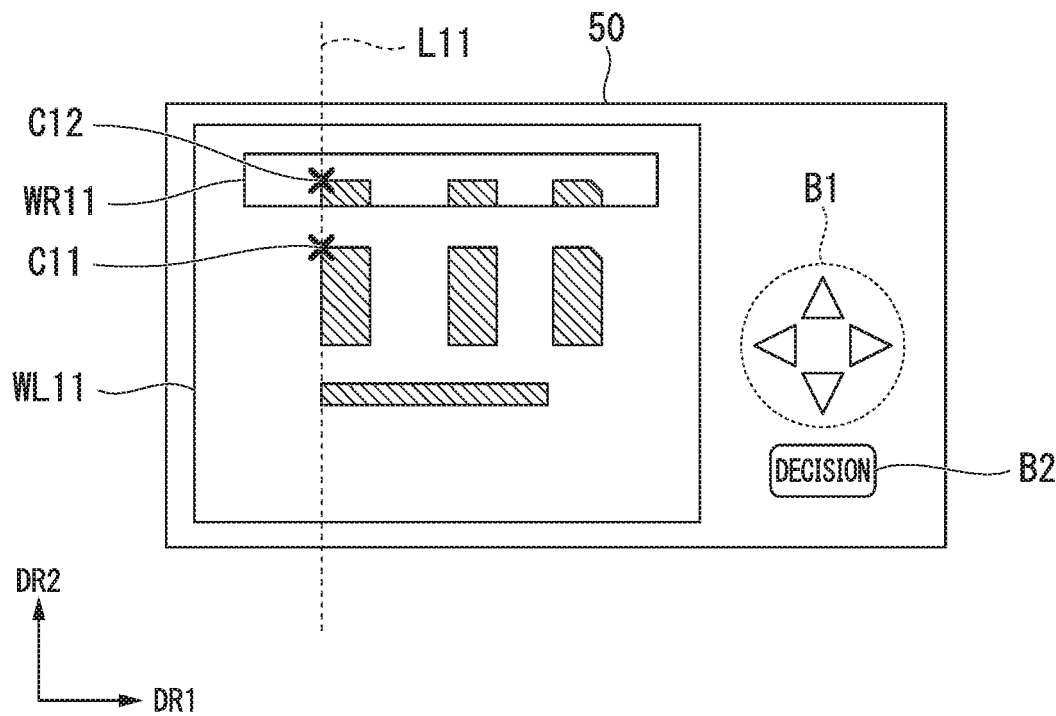
FIG. 8A is a reference diagram showing a display screen of a display unit according to the first embodiment of the present invention.
Figure 8B:
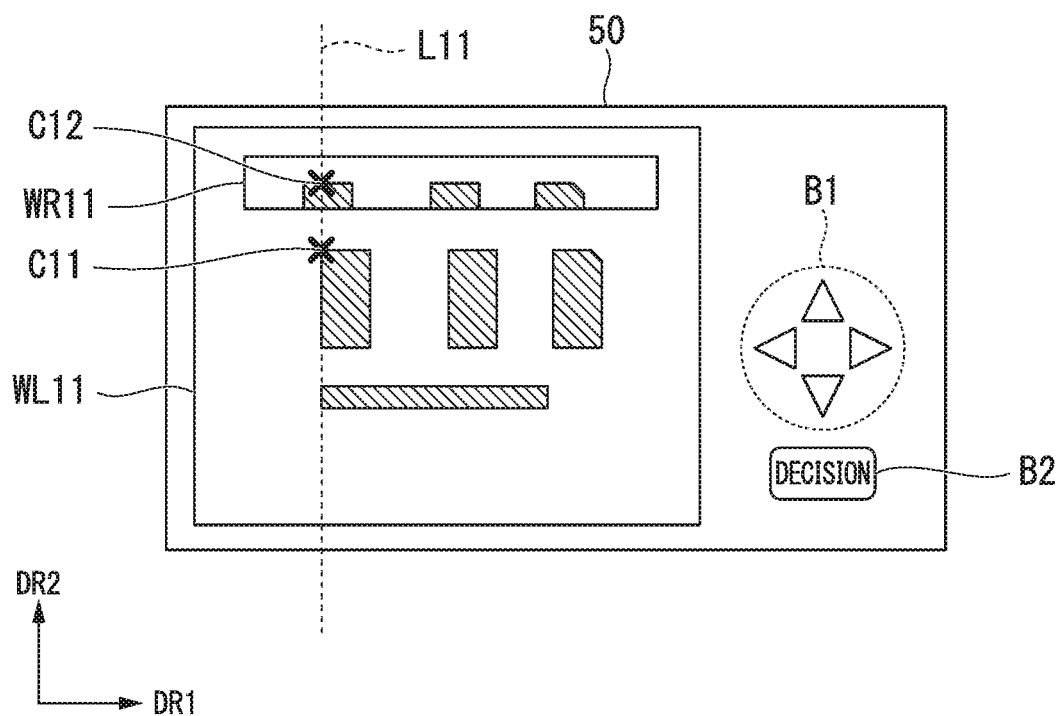
FIG. 8B is a reference diagram showing a display screen of the display unit according to the first embodiment of the present invention.

A series of flows until a position of one measurement point desired to be measured by the user is fixed will be described with reference to FIGS. 7, 8A, and 8B. FIG. 7 shows a process in a measurement mode. FIGS. 8A and 8B show display screens 50 of the display unit 5.

In the endoscopic inspection, the user checks a situation of the object from a live image and inspects whether or not there is a defect or scratches. At this time, the endoscopic measurement device 1 operates in an inspection mode. When a defect or scratches to be measured has been found from the object, a state of the endoscopic measurement device 1 moves from the inspection mode to a measurement mode.

After an operation of the measurement mode is started, the imaging device 28 images the object and acquires an imaging signal. The CCU 9 acquires a first image and a second image necessary for three-dimensional measurement as still images (step S101). The first image and the second image are output to the video signal processing circuit 12. The CPU 18a acquires the first image and the second image from the video signal processing circuit 12.

After step S101, the control unit 180 generates an image signal of a main window WL11 including the first image. The control unit 180 outputs the generated image signal to the video signal processing circuit 12. The video signal processing circuit 12 synthesizes the video signal output from the CCU 9 with the image signal output from the CPU 18a. Thereby, the main window WL11 including the first image is displayed. The video signal processing circuit 12 outputs the synthesized video signal to the display unit 5. The display unit 5 displays the main window WL11 including the first image (step S102). At this time, the second image is not displayed on the display screen 50. In the first image included in the main window WL11, a structure of the object appears. The first image displayed on the main window WL11 corresponds to a left visual field, but an image corresponding to a right visual field may be displayed as the first image in the main window WL11.

After the main window WL11 including the first image is displayed, the user determines a point and a region desired to be measured by operating the operation unit 4. For example, the operation unit 4 includes input devices such as a remote controller and a touch panel. When the user uses the remote controller, the user adjusts positions of the point and the region desired to be measured using cross keys and the like built into the remote controller. Likewise, when the user uses the touch panel, a cross button B1 or the like is used to adjust the positions of the point and the region desired to be measured. A first cursor C11 for pointing the point and the region designated by the user is displayed so that the user can visually recognize the positions of the point and the region desired to be measured by the user. The measurement point display control unit 182 causes the first cursor C11 indicating the measurement point to be displayed on the display screen 50. At this time, the measurement point display control unit 182 causes the first cursor C11 to be displayed on the first image (step S103). For example, the first cursor C11 is displayed at the center of the first image. A position at which the first cursor C11 is initially displayed may be a position other than the center of the first image. The position of the first cursor C11 is the same as the position of the measurement point in the first image. A shape and a size of the first cursor C11 are not limited.

After step S103, the measurement point detection unit 181 detects a position movement instruction from the operation unit 4 and detects a measurement point after movement. The measurement point display control unit 182 causes the position of the first cursor C11 to move on the basis of the position movement instruction. At this time, the measurement point detection unit 181 appropriately reads position information of the first cursor C11 located on the display screen 50 as a measurement point position (step S104). A measurement point thereof is a temporary measurement point whose final position has not been fixed. In the embodiment of the present invention, the temporary measurement point is treated as a measurement point in a broad sense. In the following description, a measurement point whose final position has not been fixed can be replaced with a temporary measurement point.

After step S104, a matching process for searching for a corresponding point in the second image is performed. The corresponding point is a point most similar to the measurement point, i.e., a point at which a value of a correlation with the measurement point is high. A sum of absolute differences (SAD), a sum of squared differences (SSD) and processing such as a zero-means normalized cross-correlation (ZNCC) are frequently used for the matching process. By using these matching techniques, the corresponding-point calculation unit 183 calculates a corresponding point on the second image closest to the measurement point designated on the first image (step S105).

After step S105, the corresponding-point image generation unit 184 generates a corresponding-point image that includes a corresponding point and a region in the vicinity of the corresponding point in the second image and is constituted of a part of the second image. At this time, the corresponding-point image generation unit 184 generates a corresponding-point image of which a length in a parallax direction DR1 is greater than a length in a direction DR2 orthogonal to the parallax direction DR1. That is, the corresponding-point image generation unit 184 generates a corresponding-point image elongated in the parallax direction DR1 (step S106). In FIGS. 8A and 8B, the parallax direction DR1 in the first image and the second image is a right direction. The parallax direction DR1 may be a left direction. The parallax direction DR1 is a horizontal direction (a left-right direction) on the display screen 50. In FIGS. 8A and 8B, the direction DR2 is an upward direction. The direction DR2 may be a downward direction. The direction DR2 is a vertical direction (an upward-downward direction) on the display screen 50. The corresponding-point image may include all of the second image.

After step S106, the corresponding-point image display control unit 185 generates an image signal of a sub-window WR11 including the corresponding-point image. The corresponding-point image display control unit 185 outputs the generated image signal to the video signal processing circuit 12. The video signal processing circuit 12 synthesizes the video signal output from the CCU 9 with the image signal output from the CPU 18a. Thereby, the sub-window WR11 including the corresponding-point image is displayed. The video signal processing circuit 12 outputs the synthesized video signal to the display unit 5. The display unit 5 displays the sub-window WR11 including the corresponding-point image (step S107). In the corresponding-point image included in the sub-window WR11, a structure of the object appears.

As shown in FIGS. 8A and 8B, the sub-window WR11 is superimposed on the main window WL11. In step S107, the corresponding-point image display control unit 185 causes the corresponding-point image to be displayed on the first image. At this time, the corresponding-point image display control unit 185 causes the corresponding-point image to be displayed so that all or a part of the corresponding-point image overlaps the first image. In FIGS. 8A and 8B, the entire corresponding-point image in the sub-window WR11 overlaps the first image within the main window WL11. In the main window WL11, the first image of a region where the main window WL11 and the sub-window WR11 overlap each other cannot be visually recognized. In step S107, the corresponding-point image display control unit 185 sets a display region (the sub-window WR11) of the corresponding-point image in the first image and causes the corresponding-point image to be displayed within the sub-window WR11.

In step S107, the corresponding-point image display control unit 185 causes the corresponding-point image to be displayed so that the parallax direction in the corresponding-point image is the same as the parallax direction DR1 in the first image. That is, the corresponding-point image display control unit 185 causes the corresponding-point image to be displayed so that the corresponding-point image is not inclined with respect to the first image.

In step S107, the corresponding-point image display control unit 185 causes the corresponding-point image to be displayed so that the corresponding point is separated from the measurement point. That is, the corresponding-point image display control unit 185 causes the corresponding-point image to be displayed so that positions of the corresponding point and the measurement point are different. Thereby, the user easily visually recognizes a peripheral portion of the measurement point in the first image and a peripheral portion of the corresponding point in the corresponding-point image. Also, the corresponding-point image display control unit 185 causes the corresponding-point image to be displayed so that the corresponding-point image is separated from the measurement point. That is, the corresponding-point image display control unit 185 causes the corresponding-point image to be displayed so that the corresponding-point image does not overlap the measurement point. Thereby, as described above, the user easily visually recognizes a peripheral portion of the measurement point in the first image and a peripheral portion of the corresponding point in the corresponding-point image.

In step S107, the corresponding-point image display control unit 185 causes the corresponding-point image to be displayed at the same display magnification as that of the first image. Thereby, the user easily compares an image of the vicinity of the measurement point with an image of the vicinity of the corresponding point.

After step S107, a second cursor C12 is displayed so that the user can easily check the position of the corresponding point. The corresponding-point display control unit 186 causes the second cursor C12 indicating the corresponding point to be displayed on the display screen 50. At this time, the corresponding-point display control unit 186 causes the second cursor C12 to be displayed on the corresponding-point image (step S108). The position of the second cursor C12 is the same as the position of the corresponding point in the corresponding-point image. Shapes of the first cursor C11 and the second cursor C12 are the same and sizes of the first cursor C11 and the second cursor C12 are the same. However, the present invention is not limited thereto.

As shown in FIGS. 8A and 8B, the second cursor C12 is separated from the first cursor C11 in the direction DR2. That is, the corresponding point is separated from the measurement point in the direction DR2. Because the corresponding-point image is displayed so that the corresponding-point image is separated from the measurement point, the sub-window WR11 does not overlap the first cursor C11.

After step S108, the corresponding-point image display control unit 185 adjusts a position of the corresponding-point image within the sub-window WR11. Specifically, the corresponding-point image display control unit 185 causes the corresponding-point image to be displayed so that a measurement point and a corresponding point are disposed on a straight line L11. The straight line L11 passes through the first cursor C11 and the second cursor C12. That is, the straight line L11 passes through the measurement point and the corresponding point. The straight line L11 is orthogonal to the parallax direction DR1 in the first image and the second image. Therefore, the corresponding-point image display control unit 185 adjusts the position of the corresponding-point image so that the straight line L11 passing through the measurement point and the corresponding point is orthogonal to the parallax direction DR1 on the display screen 50 (step S109). At this time, the straight line L11 is not displayed on the display screen 50.

In step S109, the measurement point display control unit 182 adjusts a position of the first cursor C11, and the corresponding-point display control unit 186 adjusts a position of the second cursor C12. That is, the measurement point display control unit 182 causes the first cursor C11 to be displayed on the straight line L11 on the display screen 50. The corresponding-point display control unit 186 causes the second cursor C12 to be displayed on the straight line L11 on the display screen 50.

Two objective optical systems (the first optical system 31 and the second optical system 32) included in the stereo-optical system (the stereo-optical adapter 30) are separated from each other in the parallax direction. A corresponding point obtained in the matching process tends to be shifted in the parallax direction with respect to a true corresponding point. The first image and the corresponding-point image are arranged so that the measurement point and the corresponding point are located on a straight line orthogonal to the parallax direction. By comparing an image of the vicinity of the measurement point with an image of the vicinity of the corresponding point, the user checks whether or not the image of the vicinity of the corresponding point has been shifted with respect to the image of the vicinity of the measurement point. Thereby, the user can easily determine whether or not erroneous matching correspondence has occurred.

FIG. 8A shows a display screen 50 of the display unit 5 when no erroneous matching correspondence has occurred. Positions indicated by the first cursor C11 and the second cursor C12 match in the object. That is, positions of the measurement point and the corresponding point match on the object. After the position of the corresponding-point image is adjusted so that the straight line L11 passing through the measurement point and the corresponding point is orthogonal to the parallax direction DR1, a position of a structure around the measurement point within the first image in the parallax direction DR1 is the same as a position of a structure around the corresponding point within the corresponding-point image. Thus, the user can determine that no erroneous matching correspondence has occurred.

FIG. 8B shows a display screen 50 of the display unit 5 when erroneous matching correspondence has occurred. Positions indicated by the first cursor C11 and the second cursor C12 do not match in the object. That is, positions of the measurement point and the corresponding point do not match on the object. Specifically, the corresponding point is shifted to a right side of the position of the measurement point in the object. After the position of the corresponding-point image is adjusted so that the straight line L11 passing through the measurement point and the corresponding point is orthogonal to the parallax direction DR1, a position of a structure around the corresponding point is shifted to a left side of a position of a structure around the measurement point within the first image. Thus, the user can determine that erroneous matching correspondence has occurred.

After step S109, the control unit 180 checks a result of determination by the user (step S110). When erroneous matching correspondence has occurred, the user moves the measurement point by operating the operation unit 4. In this case, the processing of step S104 is performed. When no erroneous matching correspondence has occurred, the user presses a decision button B2 on the display screen 50 by operating the operation unit 4. Thereby, the measurement point is fixed (step S111). Until the decision button B2 is pressed, the processing of steps S104 to S109 is iterated. By performing the processing of step S111, the process shown in FIG. 7 is completed.

When a plurality of measurement points are designated by the user, the process shown in FIG. 7 is performed for each measurement point. After all measurement points are fixed, three-dimensional coordinates of the measurement points are calculated and a size of a three-dimensional shape of the object is measured on the basis of the three-dimensional coordinates thereof.

The second cursor C12 need not be displayed in the corresponding-point image. Therefore, the CPU 18a need not have the corresponding-point display control unit 186.

It is only necessary for the sub-window WR11 to be long in the parallax direction DR1 regardless of the shape of the sub-window WR11. Although an example in which the sub-window WR11 is rectangular is shown in FIGS. 8A and 8B, the sub-window WR11 may be elliptical or polygonal.

In the first embodiment, the corresponding-point image display control unit 185 causes the corresponding-point image to be displayed on the display screen 50 so that the straight line L11 passing through the measurement point and the corresponding point is orthogonal to the parallax direction DR1. Thereby, the user can easily determine whether or not erroneous matching correspondence has occurred.

First Modified Example of First Embodiment

Figure 9:
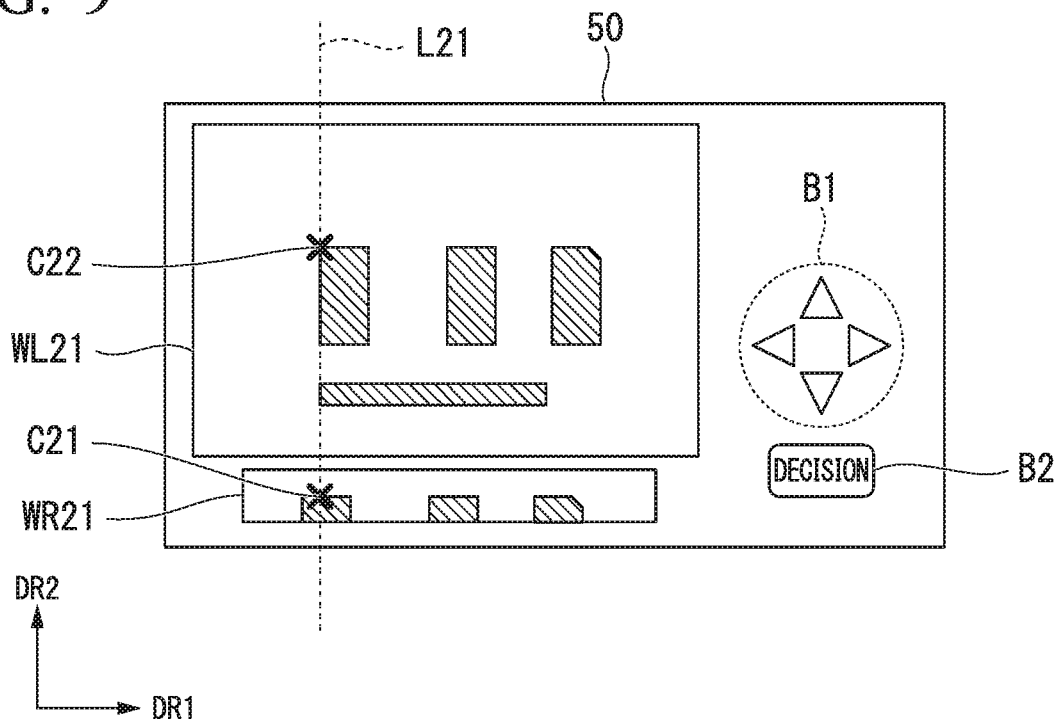
FIG. 9 is a reference diagram showing a display screen of the display unit according to a first modified example of the first embodiment of the present invention.

FIG. 9 shows a display screen 50 of the display unit 5 according to a first modified example of the first embodiment. A first image is displayed in a main window WL21 and a corresponding-point image is displayed in a sub-window WR21. A first cursor C21 indicating a measurement point and a second cursor C22 indicating a corresponding point are disposed on a straight line L21 orthogonal to the parallax direction DR1.

The control unit 180 sets a first display region (the main window WL21) of the first image and causes a first image to be displayed within the main window WL21. The corresponding-point image display control unit 185 sets a second display region (the sub-window WR21) of the corresponding-point image and causes the corresponding-point image to be displayed within the sub-window WR21. Positions of the main window WL21 and the sub-window WR21 are different. The main window WL21 and the sub-window WR21 do not overlap each other. The corresponding-point image display control unit 185 sets the sub-window WR21 below the main window WL21 on the display screen 50. On the display screen 50, the sub-window WR21 may be set above the main window WL21.

Because the main window WL21 and the sub-window WR21 do not overlap each other, the visibility of the first image does not deteriorate.

Second Modified Example of First Embodiment

Figure 10:
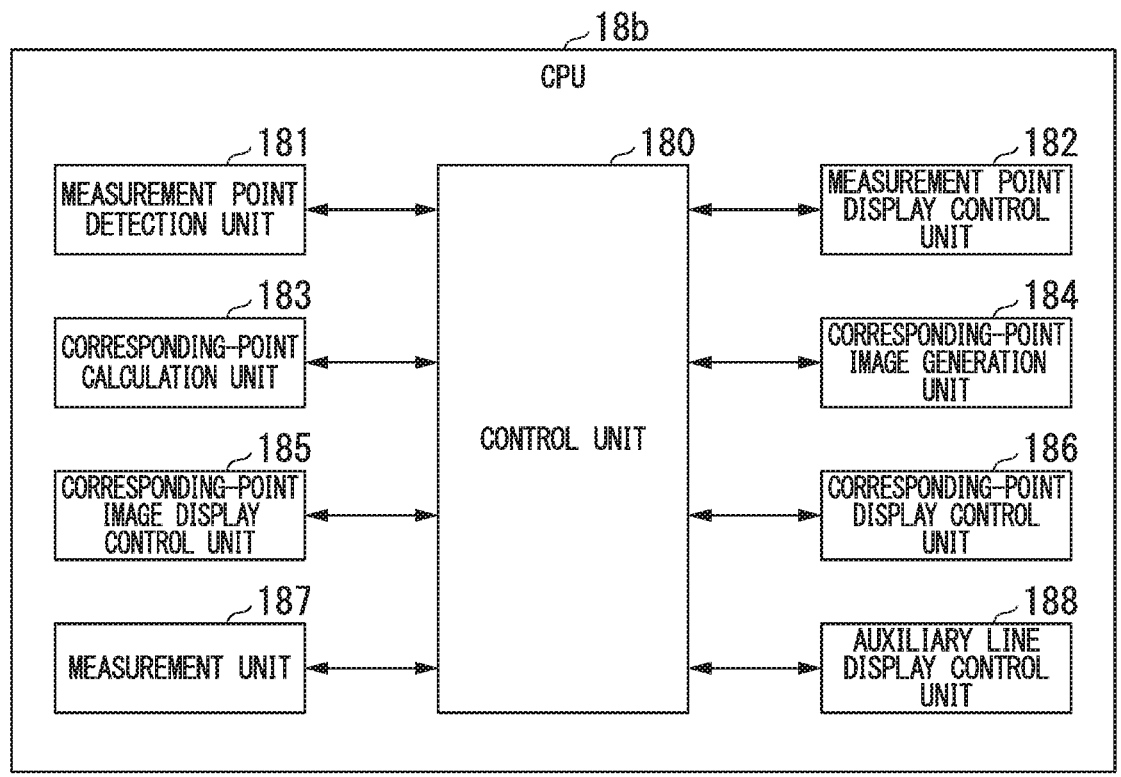
FIG. 10 is a block diagram showing a functional configuration of a CPU according to a second modified example of the first embodiment of the present invention.

In a second modified example of the first embodiment, the CPU 18a according to the first embodiment is changed to a CPU 18b shown in FIG. 10. FIG. 10 shows a functional configuration of the CPU 18b. The configuration shown in FIG. 10 will be described with respect to differences from the configuration shown in FIG. 5.

In addition to the configuration shown in FIG. 5, the CPU 18b includes an auxiliary line display control unit 188. The auxiliary line display control unit 188 causes an auxiliary line to be displayed on the display screen 50. Specifically, the auxiliary line display control unit 188 generates a graphic image signal of the auxiliary line. The auxiliary line display control unit 188 outputs the generated graphic image signal to the video signal processing circuit 12. The video signal processing circuit 12 synthesizes a video signal output from the CCU 9 with the graphic image signal output from the CPU 18b. Thereby, the auxiliary line is displayed. The video signal processing circuit 12 outputs the synthesized video signal to the display unit 5. The display unit 5 displays the auxiliary line.

Regarding points other than the above, the configuration shown in FIG. 10 is similar to the configuration shown in FIG. 5.

Figure 11:
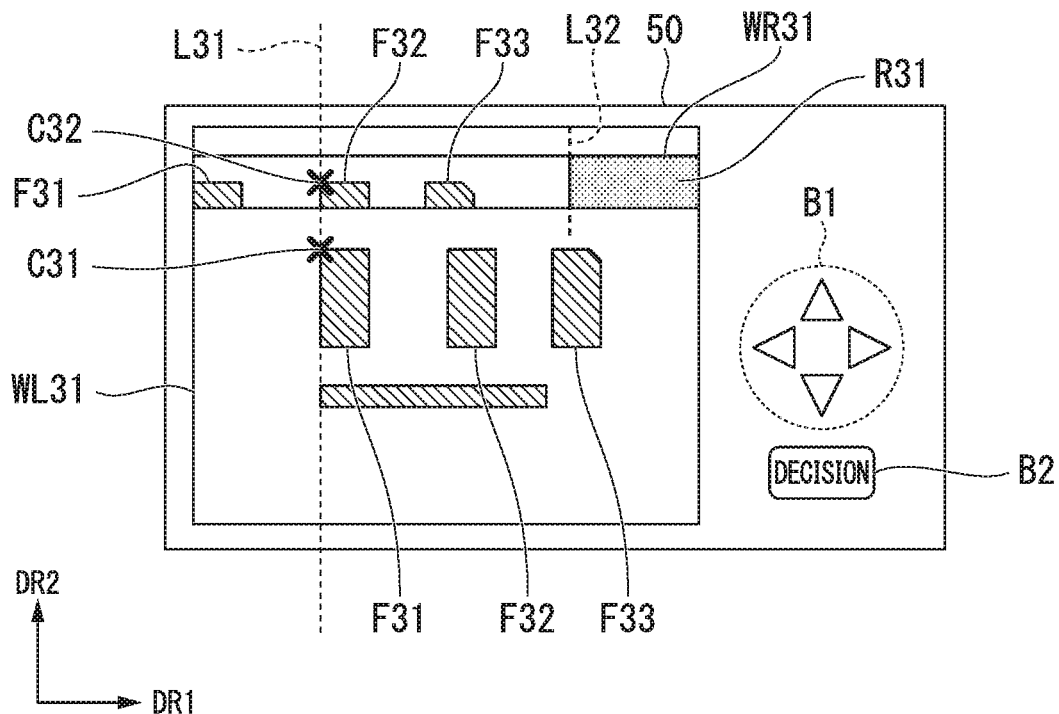
FIG. 11 is a reference diagram showing a display screen of the display unit according to the second modified example of the first embodiment of the present invention.

FIG. 11 shows a display screen 50 of the display unit 5 according to the second modified example of the first embodiment. A first image is displayed in a main window WL31 and a corresponding-point image is displayed in a sub-window WR31. A first cursor C31 indicating a measurement point and a second cursor C32 indicating a corresponding point are disposed on a straight line L31 orthogonal to the parallax direction DR1.

The corresponding-point image display control unit 185 sets a display region (the sub-window WR31) of the corresponding-point image on the display screen 50 and causes the corresponding-point image to be displayed within the sub-window WR31. When the corresponding-point image is displayed, the corresponding-point image display control unit 185 causes both end positions of the sub-window WR31 in the parallax direction DR1 to match both end positions of the first image in the parallax direction DR1, respectively. The auxiliary line display control unit 188 causes an auxiliary line L32 to be displayed so that the auxiliary line L32 passes through at least one of both ends of the corresponding-point image in the parallax direction DR1.

The length (width) of the sub-window WR31 in the parallax direction DR1 is the same as the length (width) of the first image in the parallax direction DR1. A position of a left end of the sub-window WR31 is the same as a position of a left end of the first image and a position of a right end of the sub-window WR31 is the same as a position of a right end of the first image. The corresponding-point image display control unit 185 adjusts the position of the corresponding-point image within the sub-window WR31 so that the positions of the measurement point and the corresponding-ing point are on the straight line L31.

As shown in FIG. 11, the auxiliary line L32 passes through the right end of the corresponding-point image. The auxiliary line L32 is orthogonal to the parallax direction DR1 in the first image and the second image.

Because the length of the sub-window WR31 in the parallax direction DR1 is the same as the length of the first image in the parallax direction DR1, the user can check a wide region excluding a region invisible due to parallax on a design specification of the stereo-optical adapter 30 in the corresponding-point image. Thus, the user can determine whether or not erroneous matching correspondence has occurred with reference to object information of a wider range as well as object information of a measurement point and the vicinity of a corresponding point.

For example, if the object has a periodic structure, there is a possibility that an erroneous corresponding point may be detected from another structure similar to a structure at a position of the measurement point. In FIG. 11, a measurement point is set in a structure F31 in the first image displayed in the main window WL31. Also, a corresponding point is detected from a structure F32 in the corresponding-point image displayed on the sub-window WR31. In the first image, there is no structure corresponding to the structure F31 at a position on a lower side of the structure F31 in the corresponding-point image. Also, a structure F33 in the corresponding-point image is shifted in a horizontal direction with respect to the structure F33 in the first image. Thus, the user can determine that erroneous matching correspondence has occurred.

In FIG. 11, a position of the corresponding point is significantly shifted in a right direction with respect to the position of the measurement point. The corresponding-point image display control unit 185 adjusts the position of the corresponding-point image within the sub-window WR31 and therefore the corresponding-point image is significantly shifted in the left direction with respect to the first image and displayed. The length (width) of the first image and the length (width) of the second image in the parallax direction DR1 are the same. The corresponding-point image is shifted in the left direction with respect to the first image and displayed and therefore a right end position of the corresponding-point image and a right end position of the first image do not match. A right end position of the first image matches a right end position of the sub-window WR31. Thus, a region R31 in which no image is displayed occurs between the right end of the sub-window WR31 and the right end of the corresponding-point image. In the corresponding-point image, a portion on a left side rather than a left end of the sub-window WR31 is not displayed. In addition to a result of comparing an image of the vicinity of the measurement point with an image of the vicinity of the corresponding point, a user can determine whether or not erroneous matching correspondence has occurred by referring to a result of checking an extent to which the region R31 has increased.

A background of an image acquired by the endoscope device may be frequently dark. Thus, it may be difficult to distinguish a boundary between a background of the corresponding-point image and the region R31. By displaying the auxiliary line L32, the user can easily determine an extent to which the region R31 where no image is displayed has increased. When erroneous matching correspondence does not occur and both end positions of the corresponding-point image match both end positions of the first image, two auxiliary lines may be displayed at both end positions of the corresponding-point image.

Third Modified Example of First Embodiment

In a third modified example of the first embodiment, the CPU 18a according to the first embodiment is changed to the CPU 18b shown in FIG. 10. Because FIG. 10 has already been described, a description of FIG. 10 will be omitted.

Figure 12:
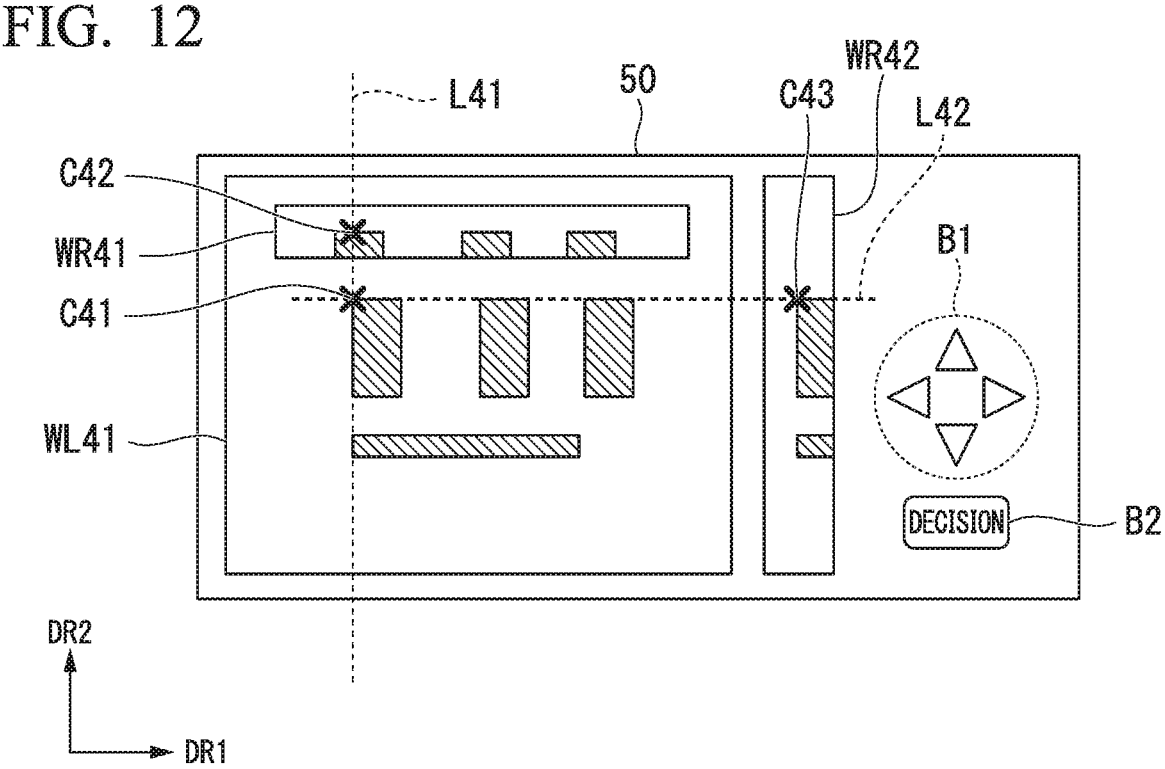
FIG. 12 is a reference diagram showing a display screen of the display unit according to a third modified example of the first embodiment of the present invention.

FIG. 12 shows a display screen 50 of the display unit 5 according to the third modified example of the first embodiment. A first image is displayed in a main window WL41 and a corresponding-point image is displayed in a sub-window WR41. A first cursor C41 indicating a measurement point and a second cursor C42 indicating a corresponding point are disposed on a straight line L41 orthogonal to the parallax direction DR1.

The corresponding-point image generation unit 184 generates a second corresponding-point image that includes a corresponding point calculated by the corresponding-point calculation unit 183 and a region in the vicinity of the corresponding point in the second image and is constituted of a part of the second image. At this time, the corresponding-point image generation unit 184 generates the second corresponding-point image of which a length in the parallax direction DR1 is less than a length in a direction DR2 orthogonal to the parallax direction DR1. That is, the corresponding-point image generation unit 184 generates the second corresponding-point image elongated in the direction DR2. The corresponding-point image display control unit 185 causes the second corresponding-point image to be displayed on the display screen 50 so that the first image and the second corresponding-point image are arranged in the parallax direction DR1.

The corresponding-point image display control unit 185 generates an image signal of a sub-window WR42 including the second corresponding-point image. The corresponding-point image display control unit 185 outputs the generated image signal to the video signal processing circuit 12. The video signal processing circuit 12 synthesizes a video signal output from the CCU 9 with the image signal output from the CPU 18b. Thereby, the sub-window WR42 including the second corresponding-point image is displayed. The video signal processing circuit 12 outputs the synthesized video signal to the display unit 5. The display unit 5 displays the sub-window WR42 including the second corresponding-point image. In the second corresponding-point image included in the sub-window WR42, a structure of the object appears.

The control unit 180 sets a first display region (the main window WL41) of the first image and causes the first image to be displayed within the main window WL41. The corresponding-point image display control unit 185 sets a second display region (the sub-window WR41) of the corresponding-point image and causes the corresponding-point image to be displayed within the sub-window WR41. Further, the corresponding-point image display control unit 185 sets a third display region (the sub-window WR42) of the second corresponding-point image and causes the second corresponding-point image to be displayed within the sub-window WR42. Positions of the main window WL41 and the sub-window WR42 are different. The main window WL41 and the sub-window WR42 do not overlap each other. The corresponding-point image display control unit 185 sets the sub-window WR42 on a right side of the main window WL41 on the display screen 50. The sub-window WR42 may be set on a left side of the main window WL41 on the display screen 50.

The length (width) of the sub-window WR42 in the parallax direction DR1 is less than the length (width) of the sub-window WR42 in the direction DR2 orthogonal to the parallax direction DR1. The length (width) of the sub-window WR42 in the direction DR2 orthogonal to the parallax direction DR1 is the same as the length (width) of the main window WL41 in the direction DR2 orthogonal to the parallax direction DR1. The corresponding-point display control unit 186 causes a third cursor C43 indicating the corresponding point to be displayed on the display screen 50. At this time, the corresponding-point display control unit 186 causes the third cursor C43 to be displayed on the second corresponding-point image. A position of the third cursor C43 is the same as a position of the corresponding point in the second corresponding-point image.

The auxiliary line display control unit 188 causes an auxiliary line L42 parallel to the parallax direction DR1 and passing through the measurement point to be displayed on the first image and the second corresponding-point image on the display screen 50. The auxiliary line L42 passes through the first cursor C41. The auxiliary line L42 may pass through the corresponding point in the second corresponding-point image or the auxiliary line L42 need not pass through the corresponding point in the second corresponding-point image.

By displaying the second corresponding-point image, the user can determine whether or not erroneous matching correspondence has occurred by referring to a wider range of object information in the direction DR2 orthogonal to the parallax direction DR1 as well as object information in the parallax direction DR1.

Fourth Modified Example of First Embodiment

Control for performing switching between display and non-display of a sub-window, i.e., a corresponding-point image, may be performed in accordance with an instruction from the user or any determination process. For example, when a movement command is continued in accordance with an operation of the operation unit 4, i.e., when a measurement point moves without stopping in a first image, the corresponding-point image display control unit 185 does not cause the sub-window, i.e., the corresponding-point image, to be displayed. Alternatively, when a movement speed of the measurement point displayed on the first image is greater than a predetermined threshold value, the corresponding-point image display control unit 185 does not cause the corresponding-point image to be displayed. When the movement speed of the measurement point displayed on the first image is less than the predetermined threshold value, the corresponding-point image display control unit 185 causes the sub-window, i.e., the corresponding-point image, to be displayed. When the measurement point has stopped for a predetermined time, for example, 1 second, the corresponding-point image display control unit 185 may cause the sub-window, i.e., the corresponding-point image, to be displayed.

Control for performing switching between display and non-display of the sub-window, i.e., the corresponding-point image, may be performed in accordance with a determination of reliability indicating whether or not the measurement point is suitable for measurement. For example, luminance of an image at a position where the measurement point is designated can be used for the determination. An index such as reliability generated in the course of a matching process may be used for the determination. For example, although the sub-window is displayed when the reliability is low, no sub-window may be displayed when the reliability is high.

The user himself/herself may issue an instruction for performing switching between display and non-display of the sub-window, i.e., the corresponding-point image. For example, when a button for performing switching between display and non-display is provided in the operation unit 4, the user inputs a display or non-display instruction by operating the button of the operation unit 4. When the display instruction has been input, the corresponding-point image display control unit 185 causes the sub-window, i.e., the corresponding-point image, to be displayed. When the non-display instruction has been input, the corresponding-point image display control unit 185 does not cause the sub-window, i.e., the corresponding-point image, to be displayed.

The user may be able to set transmittance of the sub-window. When the sub-window has been set to a transparent state, the user can check a state of the object in the first image displayed in the main window.

Fifth Modified Example of First Embodiment

A zoom function may be installed in the sub-window. That is, the corresponding-point image display control unit 185 may cause the corresponding-point image to be displayed at display magnification higher than that of the first image. Alternatively, the corresponding-point image display control unit 185 may cause the corresponding-point image to be displayed at display magnification lower than that of the first image. Using the zoom function, the user can more accurately determine whether or not erroneous matching correspondence has occurred in a state in which a range of interest is enlarged and displayed. Alternatively, the user can check a state of the entire object in a state in which the corresponding-point image is reduced and displayed.

The zoom function may be installed in the main window. That is, the corresponding-point image display control unit 185 may be able to change the display magnification of the first image. Immediately after the sub-window is displayed on the display screen 50 of the display unit 5, the zoom magnifications of the main window and the sub-window may be the same. When the zoom magnifications of the windows are equal to each other immediately after the sub-window is displayed, the user can easily check whether or not erroneous matching correspondence has occurred.

The control unit 180 and the corresponding-point image display control unit 185 may cause the zoom magnification in the main window and the zoom magnification in the sub-window to be in conjunction with each other in accordance with a magnification change instruction from the user. By causing the zoom magnifications of the windows to be in conjunction with each other, it is possible to support a task for the user to check whether or not erroneous matching correspondence has occurred.

In addition to the corresponding-point image, a depth image (a depth map) or a reliability map obtained by three-dimensional measurement may be displayed. For example, these are superimposed and displayed on the corresponding-point image. Alternatively, it may be possible to perform switching between a state in which only the corresponding-point image is displayed and a state in which only the depth image or the reliability map is displayed, by operating a button or the like.

When the reliability of a measurement value at the measurement point is low, a notification for prompting the user to pay attention may be issued. For example, colors of display frames of the main window and the sub-window displayed on the display screen 50 of the display unit 5 may change. Alternatively, a message may be displayed. Alternatively, a displayed image may be processed.

Sixth Modified Example of First Embodiment

In the first embodiment, a case in which parallax directions of two optical systems within the stereo-optical adapter 30 are the horizontal direction (the left-right direction) on the display screen 50 of the display unit 5 has been described. However, there is a case in which the parallax direction is the vertical direction (the upward-downward direction) on the display screen 50 of the display unit 5. Also in this case, the main window and the sub-window are arranged in a direction orthogonal to the parallax direction. In this regard, there is no difference from the first embodiment. However, when the parallax direction is the vertical direction on the display screen 50 of the display unit 5, the main window and the sub-window are arranged in the horizontal direction.

A case in which the parallax direction is an oblique direction different from the horizontal direction and the vertical direction on the display screen 50 of the display unit 5 is also conceivable. This case will be described below.

When the first image and the second image are not parallelized or when the optical system is designed so that the parallax direction is oblique, the parallax direction becomes oblique. When the parallax direction is oblique to the horizontal direction on the display screen 50 of the display unit 5, a straight line orthogonal to the parallax direction also becomes oblique. As in the first embodiment, when the position of the corresponding-point image is adjusted so that the measurement point and the corresponding point are disposed on the straight line orthogonal to the parallax direction, the measurement point and the correspondence point are disposed on the straight line oblique to the horizontal direction on the display screen 50 of the display unit 5. In such a specification, the user cannot easily determine whether or not matching has been correctly performed in consideration of a usage situation of a product.

Thus, when the straight line orthogonal to the parallax direction is oblique to the horizontal direction on the display screen 50 of the display unit 5 (when the parallax direction is also oblique), the measurement point and the corresponding point need not be disposed on a straight line completely orthogonal to the parallax direction. In this case, the measurement point and the corresponding point are disposed on a straight line parallel to a direction (the horizontal direction or the vertical direction) which is one of the horizontal direction and the vertical direction on the display screen 50 of the display unit 5 and which is close to the direction orthogonal to the parallax direction.

Therefore, when the direction orthogonal to the parallax direction is close to the vertical direction, the corresponding-point image display control unit 185 may cause the corresponding-point image to be displayed on the display screen 50 so that the straight line passing through the measurement point and the corresponding point is parallel to the vertical direction of the display screen 50. Alternatively, when the direction orthogonal to the parallax direction is close to the horizontal direction, the corresponding-point image display control unit 185 may cause the corresponding-point image to be displayed on the display screen 50 so that the straight line passing through the measurement point and the corresponding point is parallel to the horizontal direction of the display screen 50.

Figure 13A:
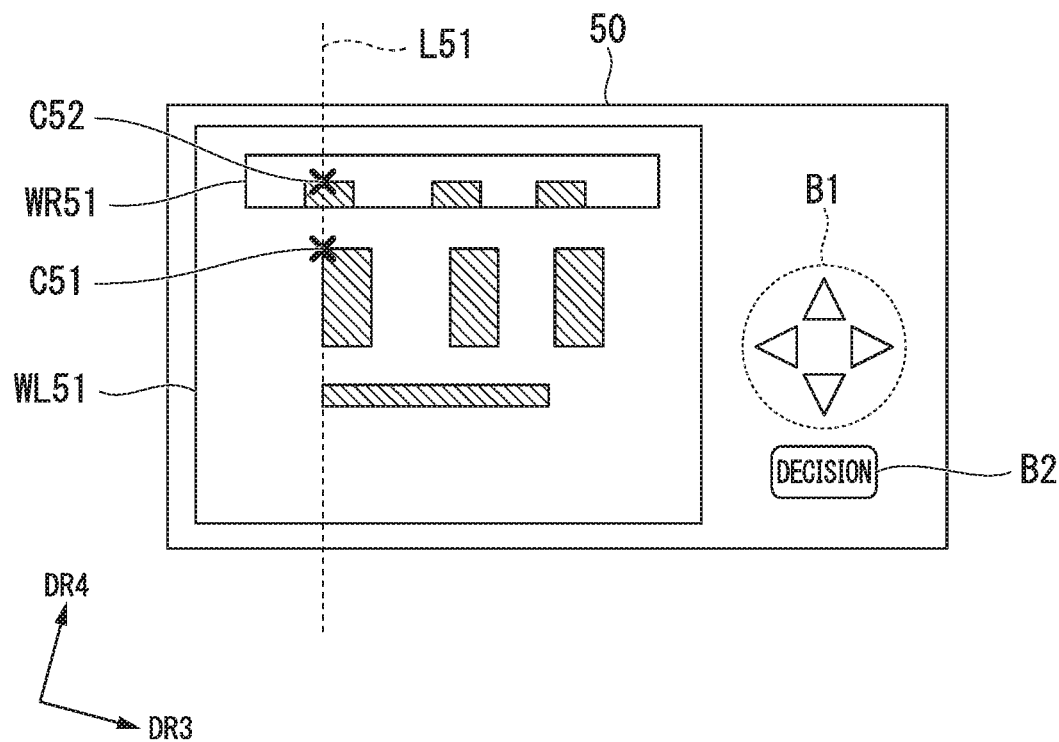
FIG. 13A is a reference diagram showing a display screen of the display unit according to a sixth modified example of the first embodiment of the present invention.
Figure 13B:
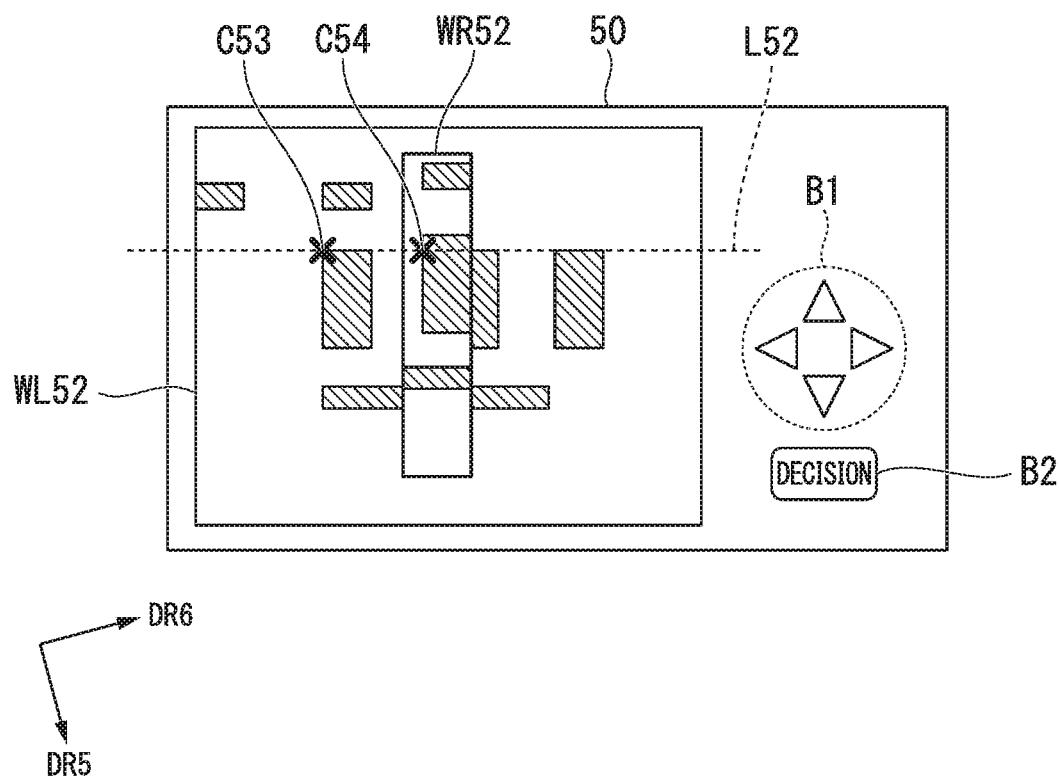
FIG. 13B is a reference diagram showing a display screen of the display unit according to the sixth modified example of the first embodiment of the present invention.

FIGS. 13A and 13B show display screens 50 of the display unit 5. As shown in FIG. 13A, a first image is displayed in a main window WL51 and a corresponding-point image is displayed in a sub-window WR51. As shown in FIG. 13B, a first image is displayed in a main window WL52 and a corresponding-point image is displayed in a sub-window WR52.

In FIG. 13A, a parallax direction DR3 does not match the horizontal direction on the display screen 50 and has an inclination with respect to the horizontal direction on the display screen 50. A direction DR4 orthogonal to the parallax direction DR3 is close to the vertical direction on the display screen 50. Thus, a corresponding-point image is displayed on the display screen 50 so that a straight line L51 passing through a measurement point and a corresponding point is parallel to the vertical direction. A first cursor C51 indicating a measurement point and a second cursor C52 indicating a corresponding point are disposed on the straight line L51.

In FIG. 13B, a parallax direction DR5 does not match the vertical direction on the display screen 50 and has an inclination with respect to the vertical direction on the display screen 50. A direction DR6 orthogonal to the parallax direction DR5 is close to the horizontal direction on the display screen 50. Thus, a corresponding-point image is displayed so that a straight line L52 passing through a measurement point and a corresponding point is parallel to the horizontal direction on the display screen 50. A first cursor C53 indicating a measurement point and a second cursor CM indicating a corresponding point are disposed on the straight line L52.

When the parallax direction is inclined by 45 degrees with respect to the horizontal direction on the display screen 50, a direction orthogonal to the parallax direction is also inclined by 45 degrees with respect to the horizontal direction on the display screen 50. In this case, a measurement point and a corresponding point are disposed on a straight line parallel to either one of the horizontal direction and the vertical direction on the display screen 50.

The parallax direction may be inclined by about several degrees with respect to the display screen 50 due to insufficient mounting of the optical adapter when the user mounts the optical adapter for measurement. Even in this case, as described above (as shown in FIG. 13A), it is only necessary for a measurement point and a corresponding point to be disposed on a straight line parallel to the vertical direction of the display screen 50 instead of a straight line completely orthogonal to the parallax direction. Thereby, the user can quickly determine whether or not erroneous matching correspondence has occurred.

Second Embodiment

A second embodiment of the present invention will be described using the endoscopic measurement device 1 shown in FIGS. 1 and 2. In the second embodiment, a display position of a corresponding-point image is adjusted so that a measurement point designated by a user in a first image matches a corresponding point in a corresponding-point image. Also, in the second embodiment, the corresponding-point image is displayed in a translucent state so that the first image can be visually recognized through the corresponding-point image.

The corresponding-point image display control unit 185 translucently processes the corresponding-point image and causes the corresponding-point image to be displayed on the first image so that the measurement point and the corresponding-point image overlap and the first image is visibly recognized through the corresponding-point image. The corresponding-point image display control unit 185 causes the corresponding-point image to be displayed on the first image so that the measurement point and the corresponding point overlap each other.

Figure 14:
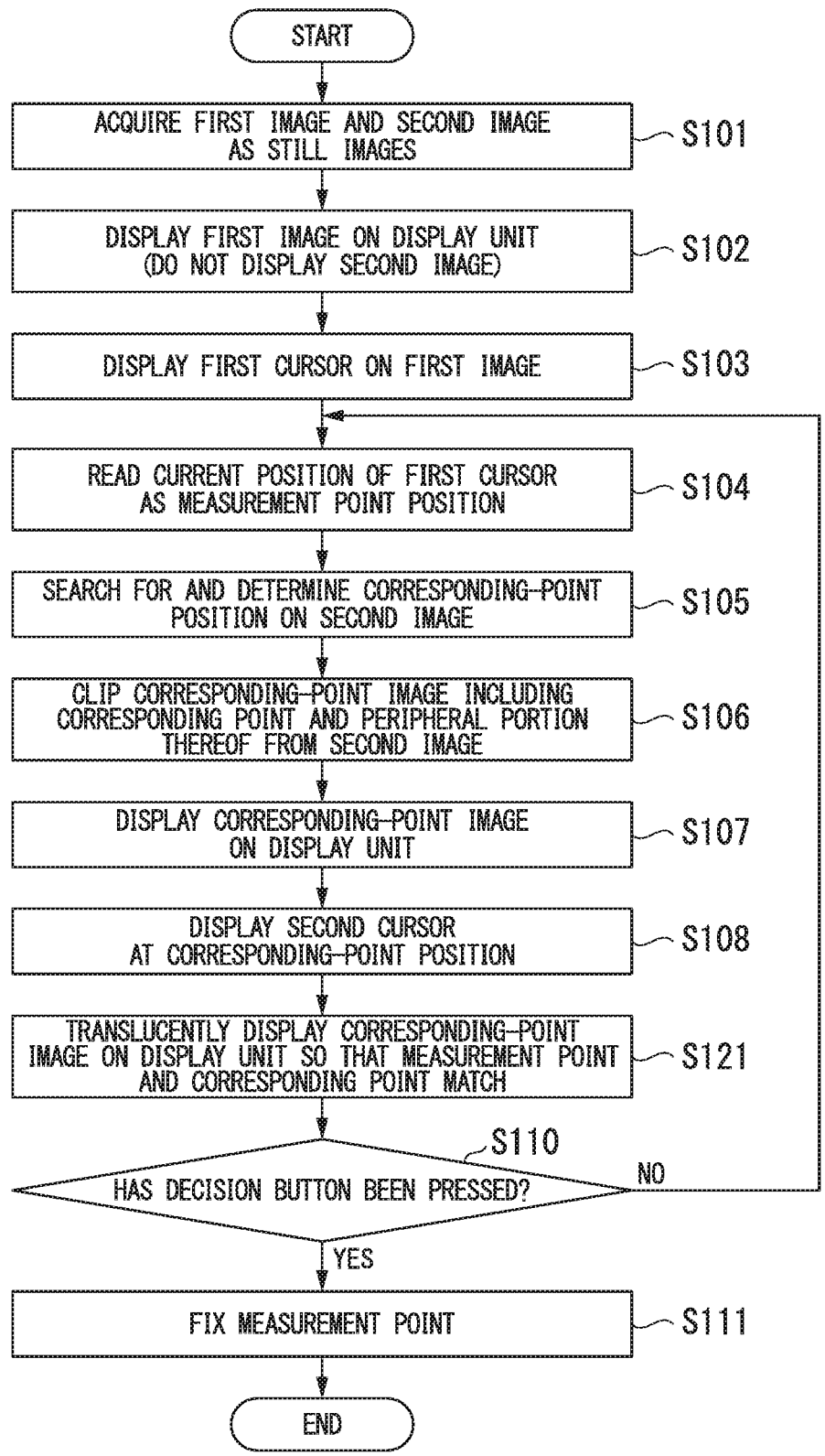
FIG. 14 is a flowchart showing a procedure of an operation of an endoscopic measurement device according to a second embodiment of the present invention.
Figure 15:
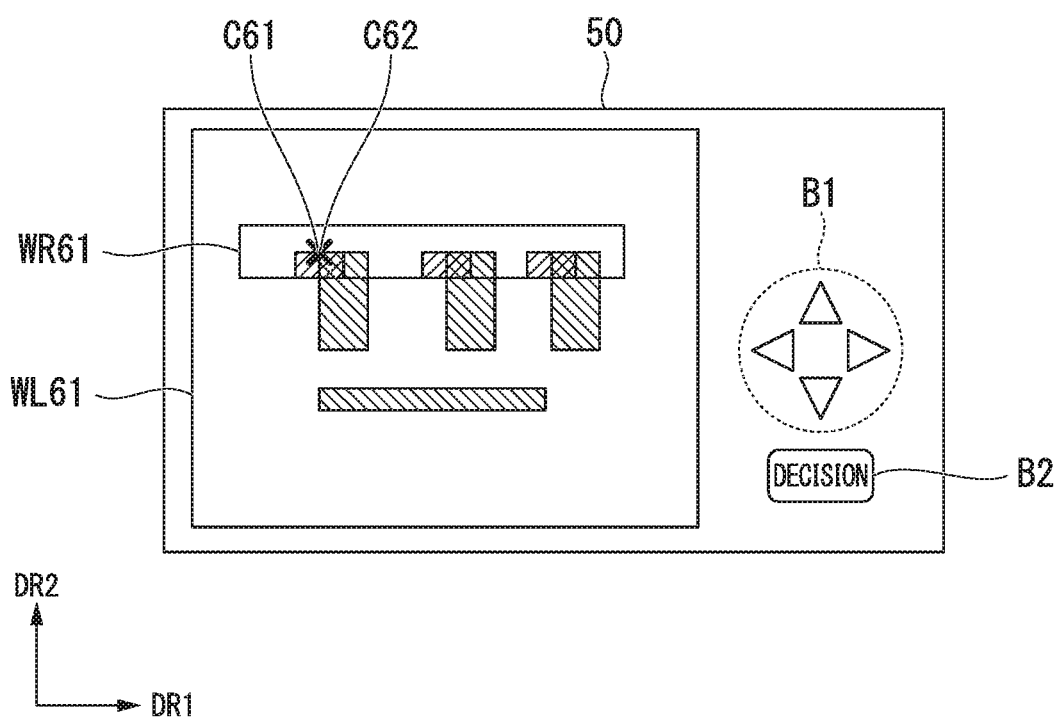
FIG. 15 is a reference diagram showing a display screen of a display unit according to the second embodiment of the present invention.

A process according to the second embodiment will be described with reference to FIGS. 14 and 15. FIG. 14 shows a process in the measurement mode. FIG. 15 shows a display screen 50 of the display unit 5. As shown in FIG. 15, a first image is displayed in a main window WL61 and a corresponding-point image is displayed in a sub-window WR61.

The process shown in FIG. 14 will be described in terms of differences from the process shown in FIG. 7. After step S108, the corresponding-point image display control unit 185 processes a corresponding-point image so that the corresponding-point image is translucent. When the corresponding-point image becomes translucent in a state in which the corresponding-point image is superimposed on the first image, both the first image and the corresponding-point image can be visibly recognized in a region where the first image and the corresponding-point image overlap each other. Further, the corresponding-point image display control unit 185 adjusts the position of the corresponding-point image in the sub-window WR61. Specifically, the corresponding-point image display control unit 185 causes the corresponding-point image to be displayed so that positions of the measurement point and the corresponding point match. Thus, a first cursor C61 indicating a measurement point and a second cursor C62 indicating a corresponding point overlap each other (step S121). After step S121, the processing of step S110 is performed.

Regarding points other than the above, the process shown in FIG. 14 is similar to the process shown in FIG. 7.

In FIG. 15, a position of a structure around the corresponding point within the corresponding point image in the sub-window WR61 is shifted to a left side of a position of a structure around the measurement point within the first image in the main window WL61. That is, erroneous matching correspondence has occurred. Because the corresponding point image is displayed in a translucent state, the user can quickly determine whether or not erroneous matching correspondence has occurred by checking a shift between both the first image and the corresponding-point image.

Third Embodiment

In a third embodiment, the CPU 18a of the first embodiment is changed to the CPU 18b shown in FIG. 10. Because FIG. 10 has already been described, a description of FIG. 10 will be omitted. In the third embodiment, one or more auxiliary lines orthogonal to a parallax direction DR1 are displayed.

An auxiliary line display control unit 188 causes the one or more auxiliary lines orthogonal to the parallax direction DR1 to be displayed on a first image and a corresponding-point image on a display screen 50. The auxiliary line display control unit 188 causes an auxiliary line to be displayed so that the auxiliary line passes through a measurement point.

Figure 16:
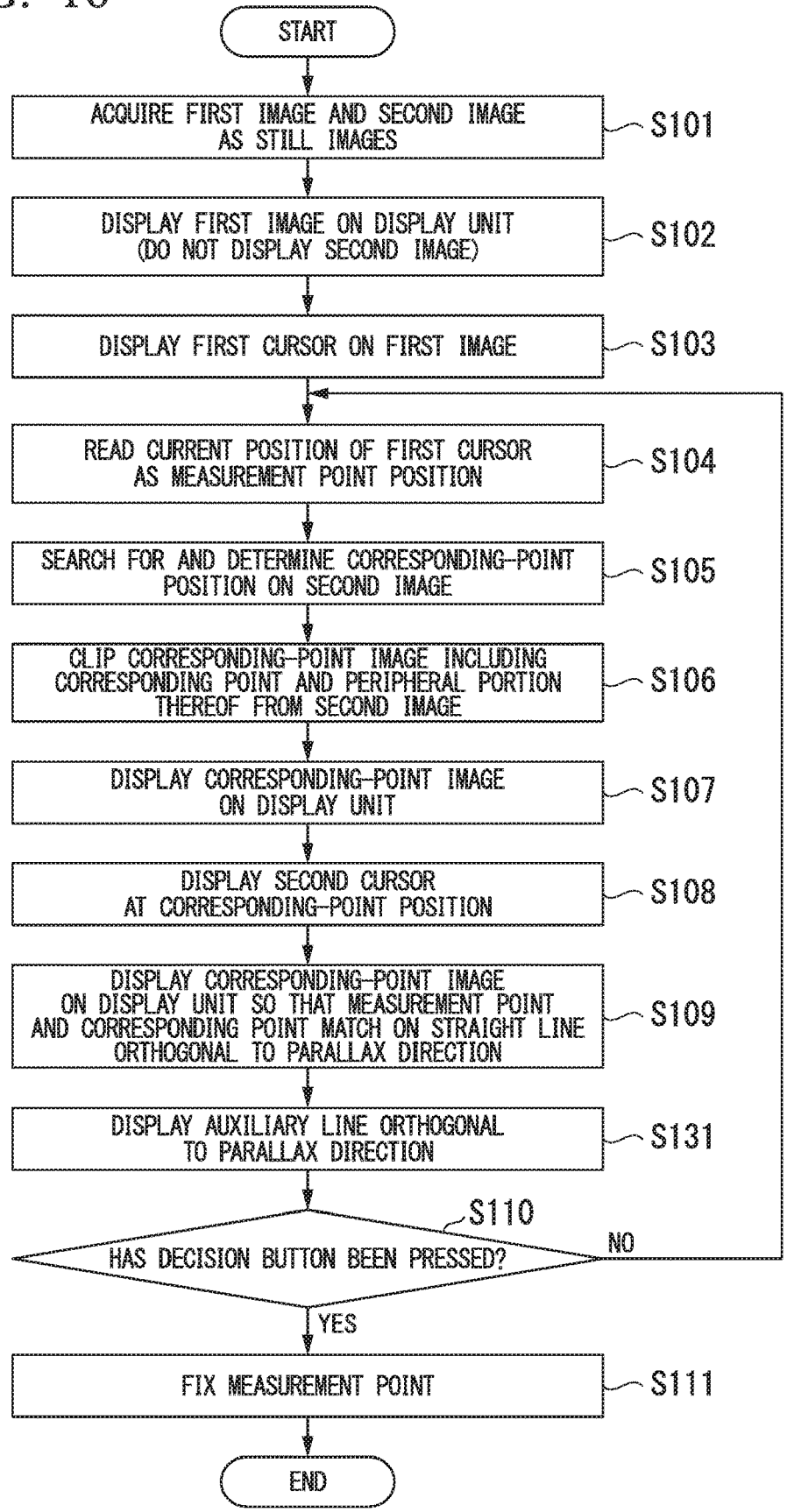
FIG. 16 is a flowchart showing a procedure of an operation of an endoscopic measurement device according to a third embodiment of the present invention.
Figure 17:
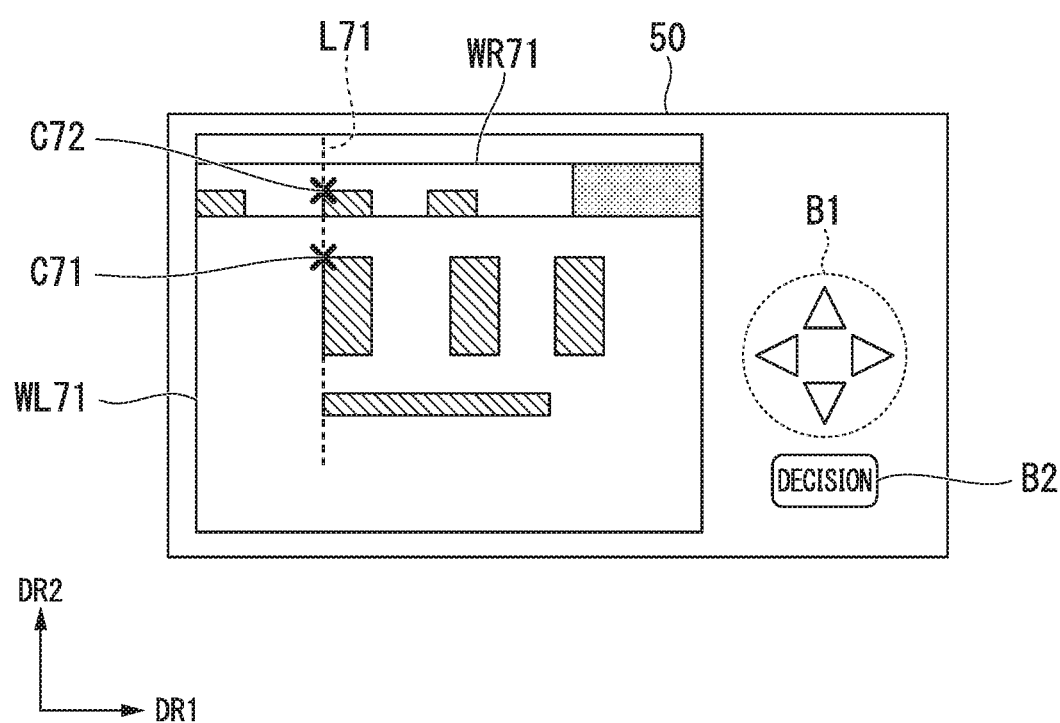
FIG. 17 is a reference diagram showing a display screen of a display unit according to the third embodiment of the present invention.

A process according to the third embodiment will be described with reference to FIGS. 16 and 17. FIG. 16 shows a process in the measurement mode. FIG. 17 shows the display screen 50 of a display unit 5. As shown in FIG. 17, a first image is displayed in a main window WL71 and a corresponding-point image is displayed in a sub-window WR71. A first cursor C71 indicating a measurement point and a second cursor C72 indicating a corresponding point are disposed on a straight line orthogonal to the parallax direction DR1.

The process shown in FIG. 16 will be described in terms of differences from the process shown in FIG. 7. After step S109, the auxiliary line display control unit 188 causes an auxiliary line L71 orthogonal to the parallax direction DR1 and passing through the measurement point to be displayed on a first image and a corresponding-point image on the display screen 50. In step S109, the corresponding-point image is displayed so that the measurement point and the corresponding point are disposed on a straight line orthogonal to the parallax direction DR1. Thus, the auxiliary line L71 orthogonal to the parallax direction DR1 passes through the measurement point and the corresponding point. That is, the auxiliary line L71 passes through the first cursor C71 and the second cursor C72. The auxiliary line display control unit 188 causes the auxiliary line to be displayed so that the auxiliary line passes through the measurement point and the corresponding point (step S131). A line type, thickness, and color of the auxiliary line L71 may be arbitrarily set. After step S131, the processing of step S110 is performed.

Regarding points other than the above, the process shown in FIG. 16 is similar to the process shown in FIG. 7.

Figure 18A:
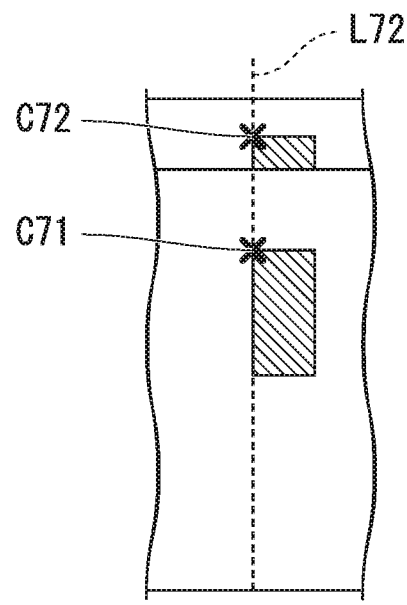
FIG. 18A is a reference diagram showing an image displayed on the display unit according to the third embodiment of the present invention.
Figure 18B:
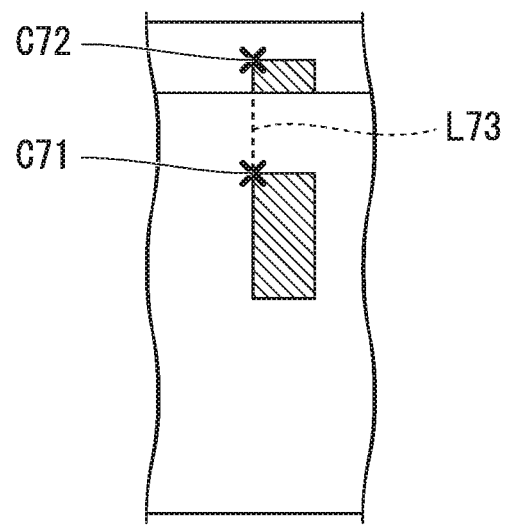
FIG. 18B is a reference diagram showing an image displayed on the display unit according to the third embodiment of the present invention.

FIGS. 18A, 18B, 18C, and 18D show various examples of auxiliary lines. An auxiliary line L72 shown in FIG. 18A is a straight line passing through the first cursor C71 and the second cursor C72. That is, the auxiliary line L72 is a straight line passing through the measurement point and the corresponding point. The auxiliary line L72 is similar to the auxiliary line L71. An auxiliary line L73 shown in FIG. 18B is a line segment passing through the first cursor C71 and the second cursor C72. That is, the auxiliary line L73 is a line segment connecting the measurement point and the corresponding point.

Figure 18C:
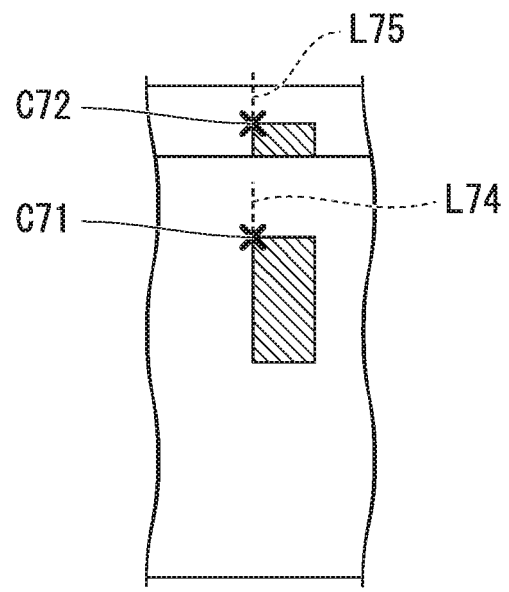
FIG. 18C is a reference diagram showing an image displayed on the display unit according to the third embodiment of the present invention.
Figure 18D:
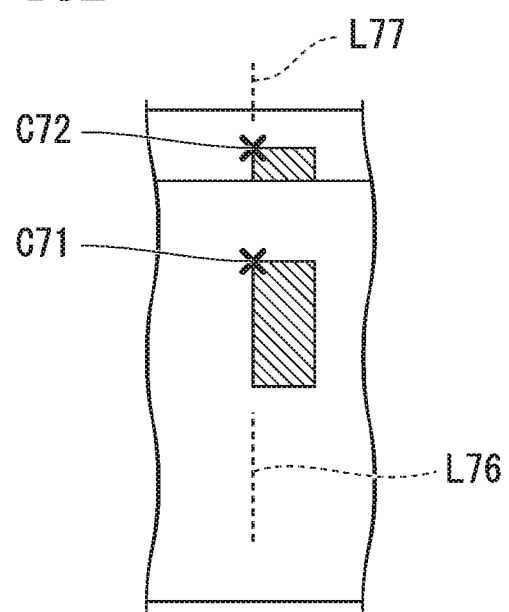
FIG. 18D is a reference diagram showing an image displayed on the display unit according to the third embodiment of the present invention.

As shown in FIGS. 18C and 18D, two or more auxiliary lines may be displayed. An auxiliary line L74 shown in FIG. 18C is a straight line passing through the first cursor C71. An auxiliary line L75 shown in FIG. 18C is a straight line passing through the second cursor C72. The auxiliary line L74 and the auxiliary line L75 do not intersect. An auxiliary line L76 and an auxiliary line L77 shown in FIG. 18D do not intersect the first cursor C71 and the second cursor C72. The auxiliary line L76 and the auxiliary line L77 are parts of a straight line passing through the first cursor C71 and the second cursor C72.

Figure 19:
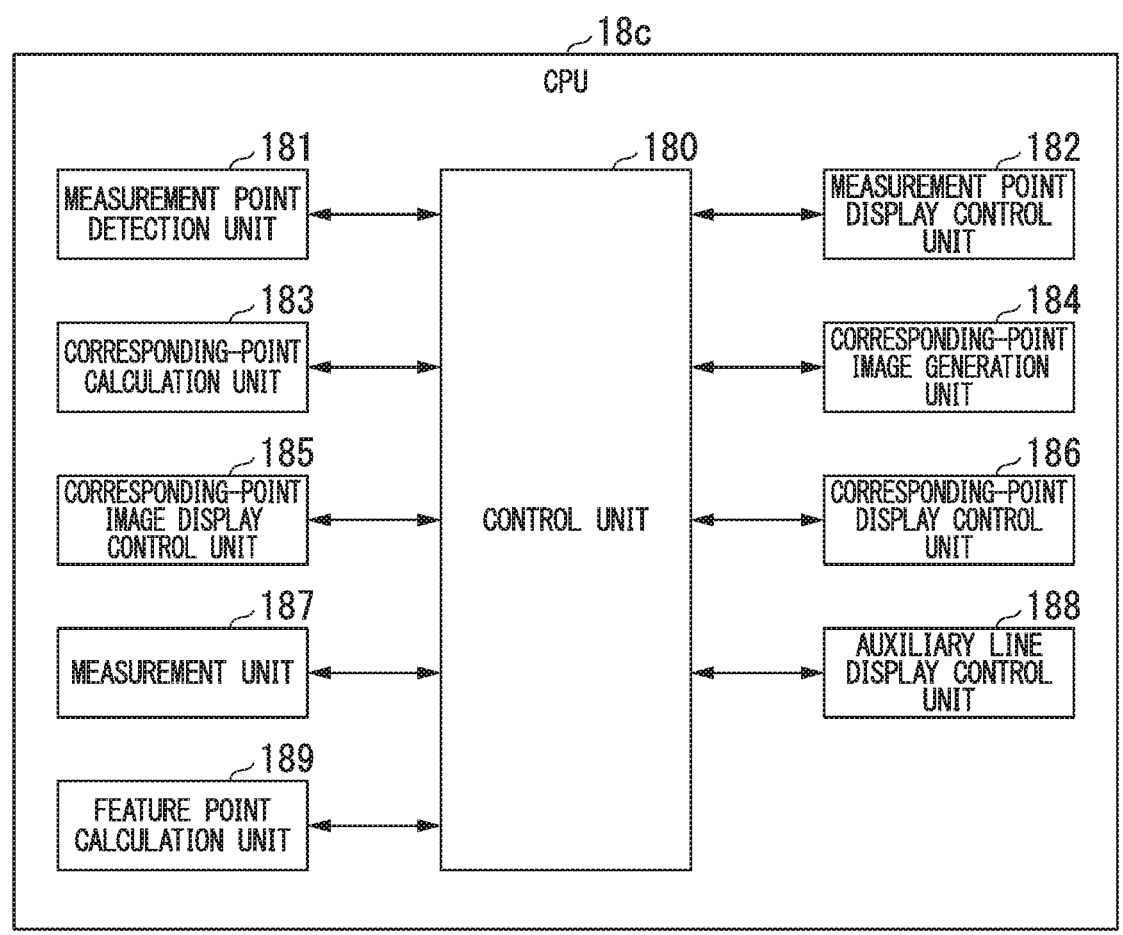
FIG. 19 is a block diagram showing a functional configuration of a CPU according to a first modified example of the third embodiment of the present invention.

In FIG. 17, a position of a structure around the corresponding point within the corresponding-point image in the sub-window WR71 is shifted to a left side of a position of a structure around the measurement point within the first image in the main window WL71. That is, erroneous matching correspondence has occurred. By comparing an image of the vicinity of the measurement point with an image of the vicinity of the corresponding point with reference to the position of the auxiliary line L71, the user easily checks whether or not the image of the vicinity of the corresponding point has been shifted with respect to the image of the vicinity of the measurement point. For example, the user can check an image shift by comparing distances from the auxiliary line L71 to characteristic structures in the first image and the corresponding-point image. Therefore, the user can easily determine whether or not erroneous matching correspondence has occurred. First Modified Example of Third Embodiment In the first modified example of the third embodiment, the CPU 18*b* is changed to a CPU 18*c* shown in FIG. 19. FIG. 19 shows a functional configuration of the CPU 18*c*. The configuration shown in FIG. 19 will be described in terms of differences from the configuration shown in FIG. 10.

In addition to the configuration shown in FIG. 10, the CPU 18*c* has a feature point calculation unit 189. The feature point calculation unit 189 calculates a first feature point other than the measurement point in the object of the first image. The auxiliary line display control unit 188 causes the auxiliary line to be displayed so that the auxiliary line passes through the first feature point. Also, the feature point calculation unit 189 calculates a second feature point other than the corresponding point in the object of the corresponding-point image. The auxiliary line display control unit 188 causes an auxiliary line to be displayed so that the auxiliary line passes through the second feature point.

Regarding points other than the above, the configuration shown in FIG. 19 is similar to the configuration shown in FIG. 10.

Figure 20:
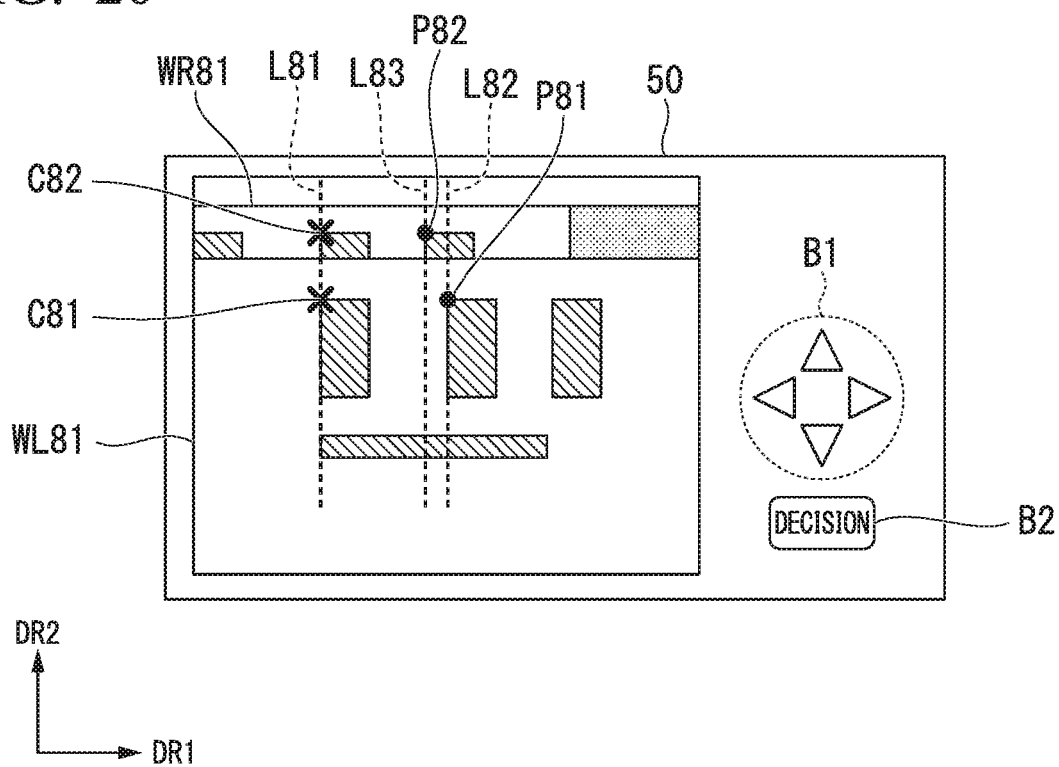
FIG. 20 is a reference diagram showing a display screen of the display unit according to the first modified example of the third embodiment of the present invention.

FIG. 20 shows a display screen 50 of the display unit 5. As shown in FIG. 20, a first image is displayed in a main window WL81 and a corresponding-point image is displayed in a sub-window WR81. A first cursor C81 indicating a measurement point and a second cursor C82 indicating a corresponding point are disposed on a straight line orthogonal to the parallax direction DR1.

The auxiliary line display control unit 188 causes an auxiliary line L81 passing through the first cursor C81 and the second cursor C82 to be displayed. The feature point calculation unit 189 calculates a feature point P81 of the object from the image of the vicinity of the measurement point in the first image. For example, as a method of calculating a feature point, there are methods using a Harris feature quantity, a SIFT feature quantity, a FAST feature quantity, and the like. Although one feature point P81 in the first image is calculated in FIG. 20, a plurality of feature points may be calculated. The auxiliary line display control unit 188 causes an auxiliary line L82 orthogonal to the parallax direction DR1 and passing through the feature point P81 to be displayed. The auxiliary line L82 is parallel to the auxiliary line L81.

The feature point calculation unit 189 calculates a feature point P82 of the object from an image of the vicinity of the corresponding point in the corresponding-point image. Although one feature point P82 in the corresponding-point image is calculated in FIG. 20, a plurality of feature points may be calculated. The auxiliary line display control unit 188 causes an auxiliary line L83 orthogonal to the parallax direction DR1 and passing through the feature point P82 to be displayed. The auxiliary line L83 is parallel to the auxiliary line L81. Only one of the feature point P81 and the feature point P82 may be detected and only one of the auxiliary line L82 and the auxiliary line L83 may be displayed.

Figure 21:
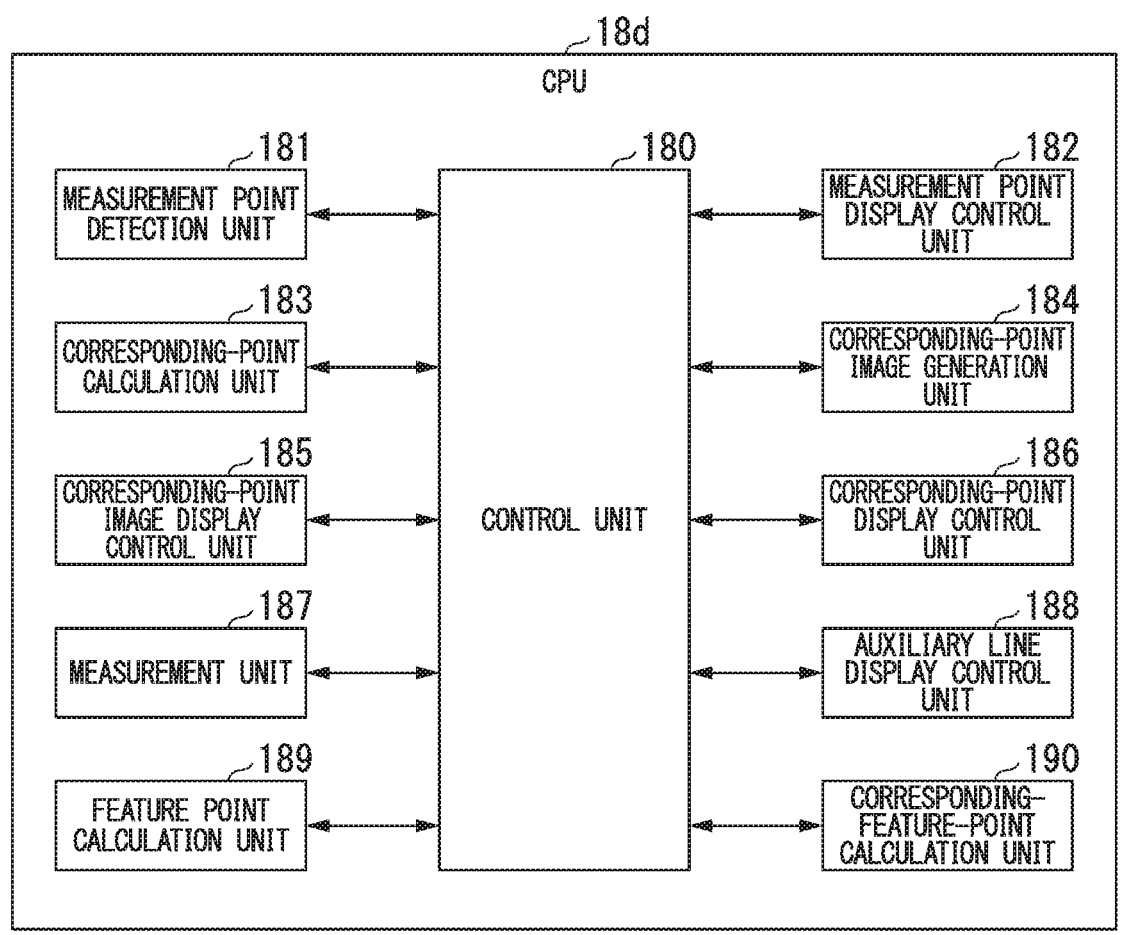
FIG. 21 is a block diagram showing a functional configuration of the CPU according to a second modified example of the third embodiment of the present invention.

In FIG. 20, a position of a structure around the corresponding point within the corresponding-point image in the sub-window WR81 is shifted to a left side of a position of a structure around the measurement point within the first image in the main window WL81. That is, erroneous matching correspondence has occurred. Because the auxiliary line L82 and the auxiliary line L83 are displayed, the user can easily check a peripheral portion of the measurement point in the first image and a peripheral portion of the corresponding point in the corresponding-point image. For example, the user can check an image shift by comparing a structure on the auxiliary line L82 or the auxiliary line L83 in the first image with a structure on the auxiliary line L82 or the auxiliary line L83 in the corresponding-point image. Thus, the user can easily determine whether or not erroneous matching correspondence has occurred. Second Modified Example of Third Embodiment In a second modified example of the third embodiment, the CPU 18c is changed to a CPU 18d shown in FIG. 21. FIG. 21 shows a functional configuration of the CPU 18d. The configuration shown in FIG. 21 will be described in terms of differences from the configuration shown in FIG. 19.

In addition to the configuration shown in FIG. 19, the CPU 18d includes a corresponding-feature-point calculation unit 190. The feature point calculation unit 189 calculates a feature point other than a measurement point in an object of a first image. The corresponding-feature-point calculation unit 190 calculates a corresponding feature point on a second image corresponding to the feature point on the first image. The auxiliary line display control unit 188 causes an auxiliary line passing through the feature point and the corresponding feature point to be displayed.

Regarding points other than the above, the configuration shown in FIG. 21 is similar to the configuration shown in FIG. 19.

Figure 22:
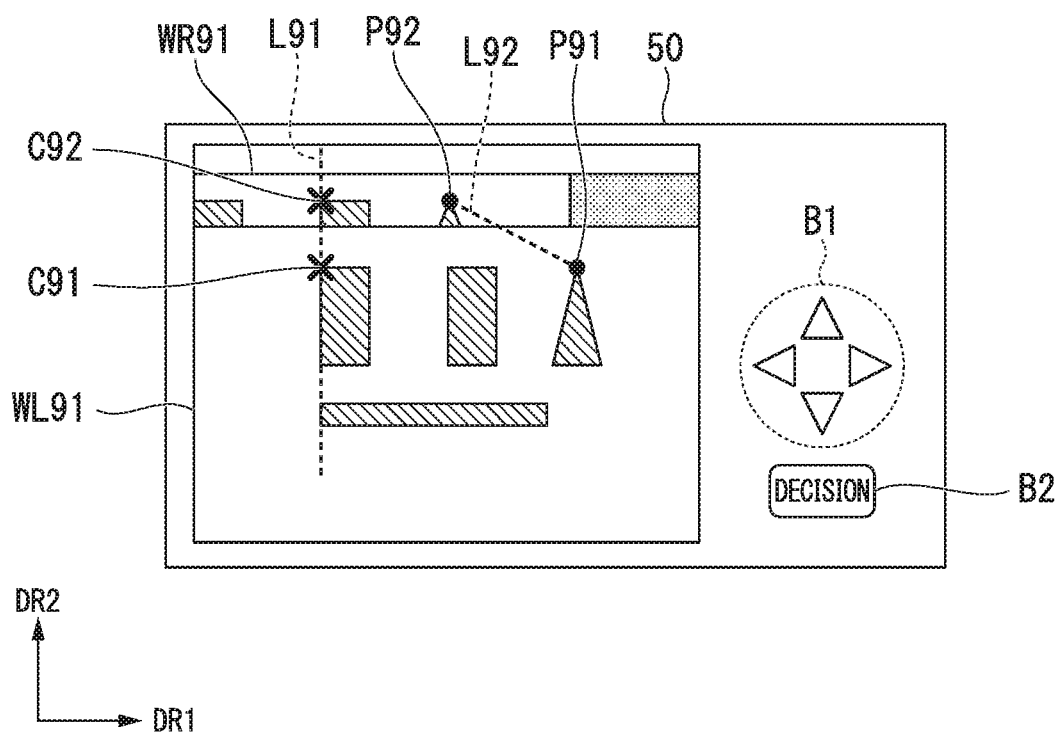
FIG. 22 is a reference diagram showing a display screen of the display unit according to a second modified example of the third embodiment of the present invention.

FIG. 22 shows a display screen 50 of the display unit 5. As shown in FIG. 22, a first image is displayed in a main window WL91 and a corresponding-point image is displayed in a sub-window WR91. A first cursor C91 indicating a measurement point and a second cursor C92 indicating a corresponding point are disposed on a straight line orthogonal to the parallax direction DR1.

The auxiliary line display control unit 188 causes an auxiliary line L91 passing through the first cursor C91 and the second cursor C92 to be displayed. The feature point calculation unit 189 calculates a feature point P91 of an object from an image of the vicinity of the measurement point in the first image. Although one feature point P91 in the first image is calculated in FIG. 22, a plurality of feature points may be calculated. The corresponding-feature-point calculation unit 190 calculates a feature point P92 (a corresponding feature point) of the object from an image of the vicinity of the corresponding point in the corresponding-point image. Although one feature point P92 in the corresponding-point image is calculated in FIG. 22, a plurality of feature points may be calculated. The corresponding-feature-point calculation unit 190 performs matching between the feature point P91 and the feature point P92 and determines whether or not features of the image at the feature point P91 and the feature point P92 are similar. When it is determined that the features are similar, the corresponding-feature-point calculation unit 190 determines that the feature point P91 and the feature point P92 are the same point. That is, the corresponding-feature-point calculation unit 190 determines that the feature point P92 is a corresponding feature point of the feature point P91. There may be a plurality of corresponding feature points. The auxiliary line display control unit 188 causes an auxiliary line L92 passing through the feature point P91 and the feature point P92 determined to be the same point to be displayed.

In FIG. 22, the measurement point indicated by the first cursor C91 is located in a rectangle located at a left side of a rectangle closest to a triangle. The corresponding point indicated by the second cursor C92 is located in a rectangle closest to a triangle. Therefore, the measurement point and the corresponding point do not match. That is, erroneous matching correspondence has occurred. By comparing an image of the vicinity of the measurement point with an image of the vicinity of the corresponding point with reference to a position of the auxiliary line L92, the user can easily check whether or not the image of the vicinity of the corresponding point is shifted with respect to the image of the vicinity of the measurement point. For example, because the auxiliary line L92 is not vertical but is oblique, the user can check an image shift. Thus, the user can easily determine whether or not erroneous matching correspondence has occurred.

Fourth Embodiment

A fourth embodiment of the present invention will be described using the endoscopic measurement device 1 shown in FIGS. 1 and 2. In the fourth embodiment, a display position of a sub-window is switched in accordance with a position of a measurement point in a first image displayed in a main window.

The corresponding-point image display control unit 185 controls a display position of the corresponding-point image in accordance with the position of the measurement point. In the first image, the corresponding-point image display control unit 185 sets a plurality of image regions arranged in a direction DR2 orthogonal to a parallax direction DR1. The plurality of image regions include a first image region and a second image region. A direction orthogonal to the parallax direction DR1 and directed from the first image region to the second image region is a first direction. A direction orthogonal to the parallax direction DR1 and directed from the second image region to the first image region is a second direction. When the measurement point is located within the first image region, the corresponding-point image display control unit 185 causes the corresponding-point image to be displayed at a position on the first direction side of the measurement point. When the measurement point is located within the second image region, the corresponding-point image display control unit 185 causes the corresponding-point image to be displayed at a position on the second direction side of the measurement point. The corresponding-point image display control unit 185 causes the corresponding-point image to be displayed on the first image.

Figure 23:
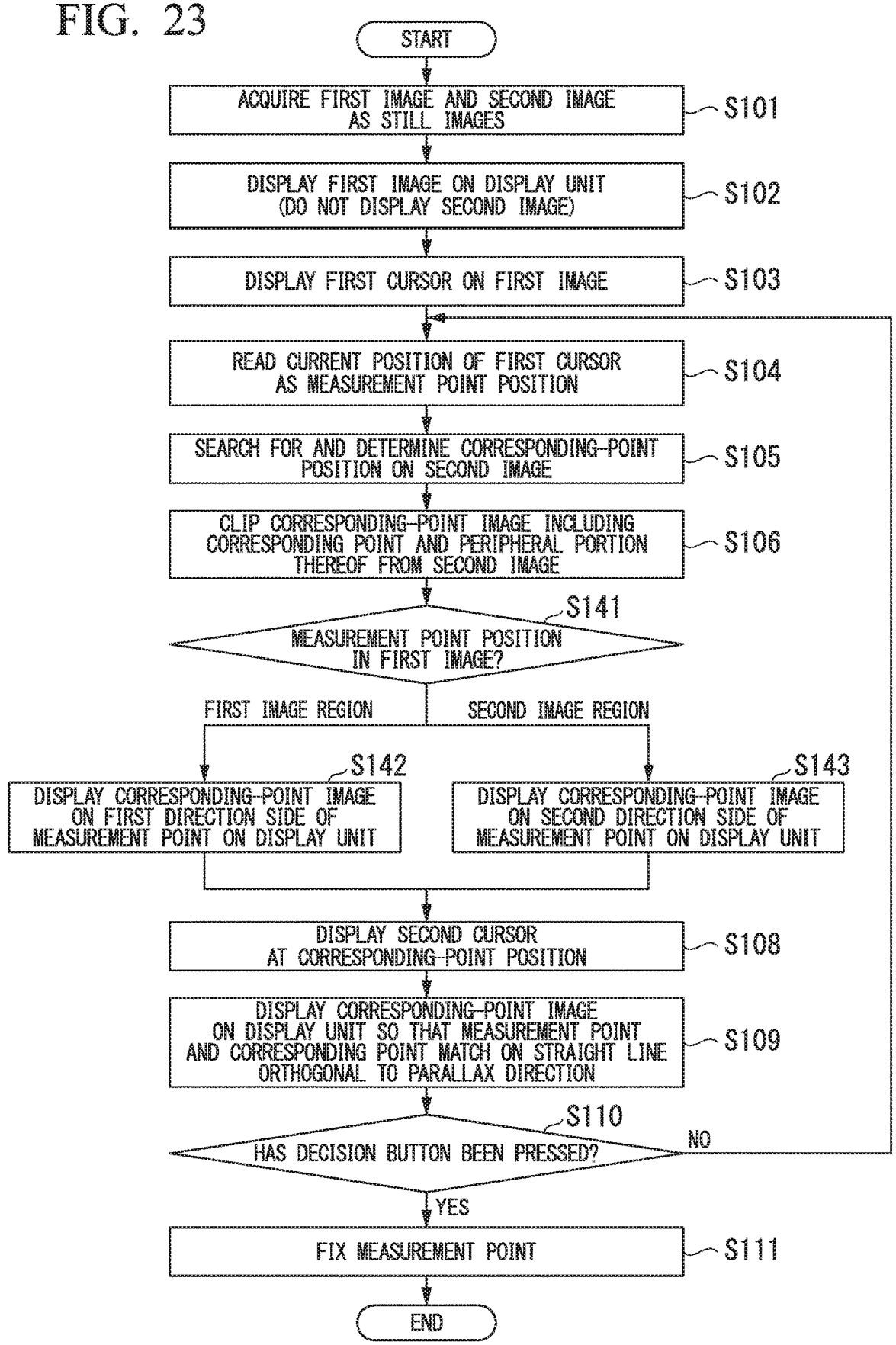
FIG. 23 is a flowchart showing a procedure of an operation of an endoscopic measurement device according to a fourth embodiment of the present invention.
Figure 24A:
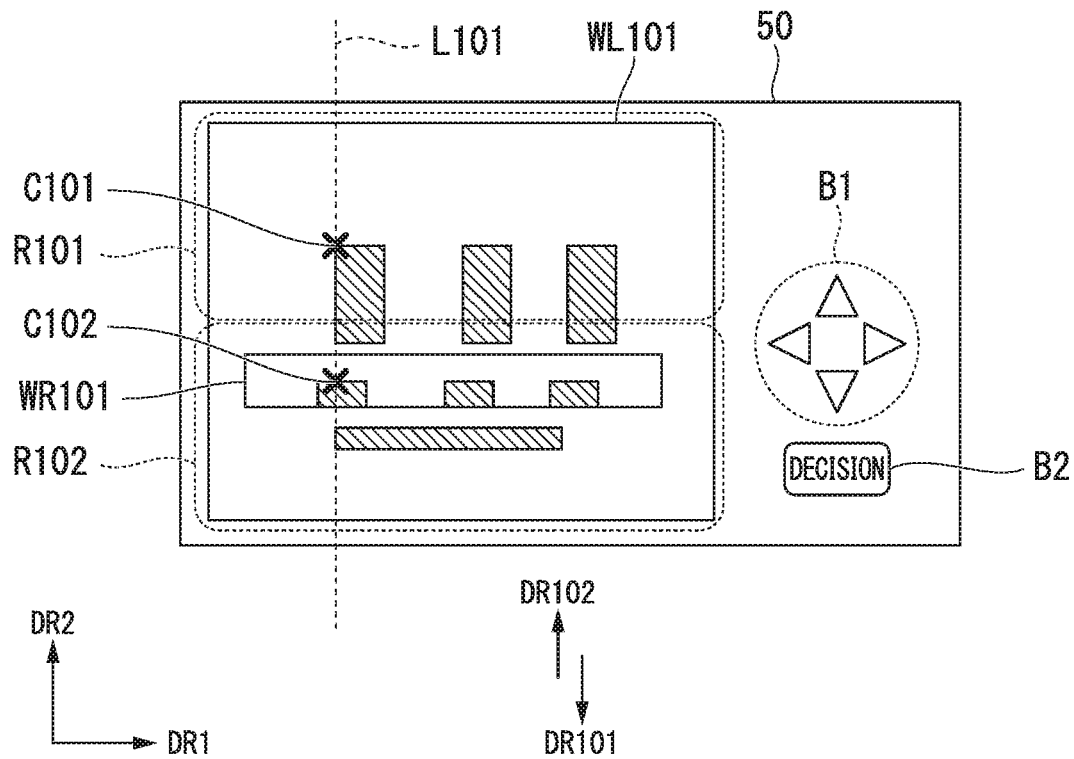
FIG. 24A is a reference diagram showing a display screen of a display unit according to the fourth embodiment of the present invention.
Figure 24B:
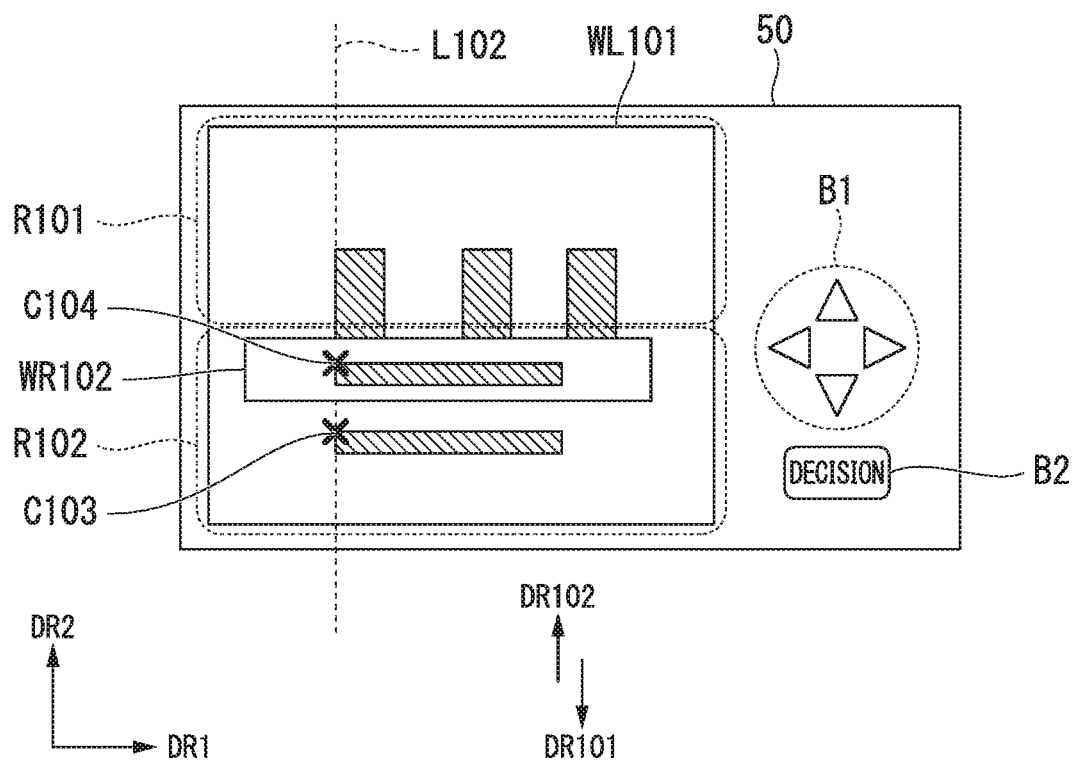
FIG. 24B is a reference diagram showing a display screen of the display unit according to the fourth embodiment of the present invention.

A process according to the fourth embodiment will be described with reference to FIGS. 23, 24A, and 24B. FIG. 23 shows a process in the measurement mode. FIGS. 24A and 24B show display screens 50 of the display unit 5.

The corresponding-point image display control unit 185 presets a first image region R101 and a second image region R102 in the first image displayed in a main window WL101. The first image region R101 and the second image region R102 are arranged in a direction DR2 orthogonal to the parallax direction DR1. In FIGS. 24A and 24B, the first image includes only the first image region R101 and the second image region R102. Although areas of the first image region R101 and the second image region R102 are the same in FIGS. 24A and 24B, the areas of the first image region R101 and the second image region R102 may be different. In FIGS. 24A and 24B, a first direction DR101 and a second direction DR102 are defined. The first direction DR101 is a direction that is orthogonal to the parallax direction DR1 and is directed from the first image region R101 to the second image region R102. The second direction DR102 is a direction that is orthogonal to the parallax direction DR1 and is directed from the second image region R102 to the first image region R101. The second direction DR102 is opposite to the first direction DR101.

A process shown in FIG. 23 will be described in terms of differences from the process shown in FIG. 7. After step S106, the corresponding-point image display control unit 185 determines a position of a measurement point read in step S104 (step S141). When the measurement point is located within the first image region R101, the corresponding-point image display control unit 185 causes a corresponding-point image to be displayed at a position on the first direction DR101 side of the measurement point (step S142). When the measurement point is located within the second image region R102, the corresponding-point image display control unit 185 causes the corresponding-point image to be displayed at a position on the second direction DR102 side of the measurement point (step S143). After step S142 or step S143, the processing of step S108 is performed.

In step S142, even if the measurement point is in the first image region R101, the corresponding-point image is not necessarily displayed in the second image region R102. Also, even if the measurement point is located in the second image region R102 in step S143, the corresponding-point image is not necessarily displayed in the first image region R101. A position where the corresponding-point image is displayed in step S142 and step S143 may be either the first image region R101 or the second image region R102. Also, a position where the corresponding-point image is displayed in steps S142 and S143 may be a region different from the first image region R101 and the second image region R102. That is, a position where the corresponding-point image is displayed in steps S142 and S143 may be a region outside the first image.

Regarding points other than the above, the process shown in FIG. 23 is similar to the process shown in FIG. 7.

As shown in FIG. 24A, a first cursor C101 indicating a measurement point is located within the first image region R101. Thus, in step S142, the corresponding-point image display control unit 185 causes the corresponding-point image to be displayed at a position on the first direction DR101 side of the first cursor C101. A sub-window WR101 including the corresponding-point image is displayed at a position on the first direction DR101 side of the first cursor C101. In the fourth embodiment, the sub-window WR101 is displayed in the second image region R102. The length (width) of the sub-window WR101 in the direction DR2 orthogonal to the parallax direction DR1 is less than the length (width) of each of the first image region R101 and the second image region R102 in the direction DR2. The first cursor C101 and the second cursor C102 are disposed on a straight line L101 orthogonal to the parallax direction DR1. The sub-window WR101 is not necessarily displayed in the second image region R102. According to a position of the first cursor C101, the sub-window WR101 may be displayed within the first image region R101.

As shown in FIG. 24B, a first cursor C103 indicating a measurement point is located within the second image region R102. Thus, in step S143, the corresponding-point image display control unit 185 causes a corresponding-point image to be displayed at a position on the second direction DR102 side of the first cursor C103. A sub-window WR102 including the corresponding-point image is displayed at a position on the second direction DR102 side of the first cursor C103. In the fourth embodiment, the sub-window WR102 is displayed in the first image region R101. The length (width) of the sub-window WR102 in the direction DR2 orthogonal to the parallax direction DR1 is less than the length (width) of each of the first image region R101 and the second image region R102 in the direction DR2. The first cursor C103 and the second cursor C104 are disposed on a straight line L102 orthogonal to the parallax direction DR1.

In FIGS. 24A and 24B, two image regions are set. Three or more image regions may be set. When the three or more image regions are set, two of the three or more regions are the first image region and the second image region. Also, a plurality of image regions may be changeable as necessary.

As described above, a corresponding-point image is displayed at a position on the first direction DR101 side or the second direction DR102 side of the measurement point in accordance with a position of the measurement point. Thus, it is possible to display the corresponding-point image at a position which is hardly limited by a size of the display screen 50 of the display unit 5. That is, it is possible to display a corresponding-point image at a position where the corresponding-point image is easily viewed.

First Modified Example of Fourth Embodiment

According to a first modified example of the fourth embodiment, the corresponding-point image display control unit 185 sets a plurality of image regions arranged in the direction DR2 orthogonal to the parallax direction DR1 in a first image. The plurality of image regions include a first image region and a second image region. When a measurement point is located within the first image region, the corresponding-point image display control unit 185 causes a corresponding-point image to be displayed in the first image region. When the measurement point is located within the second image region, the corresponding-point image display control unit 185 causes the corresponding-point image to be displayed in the second image region.

Figure 25A:
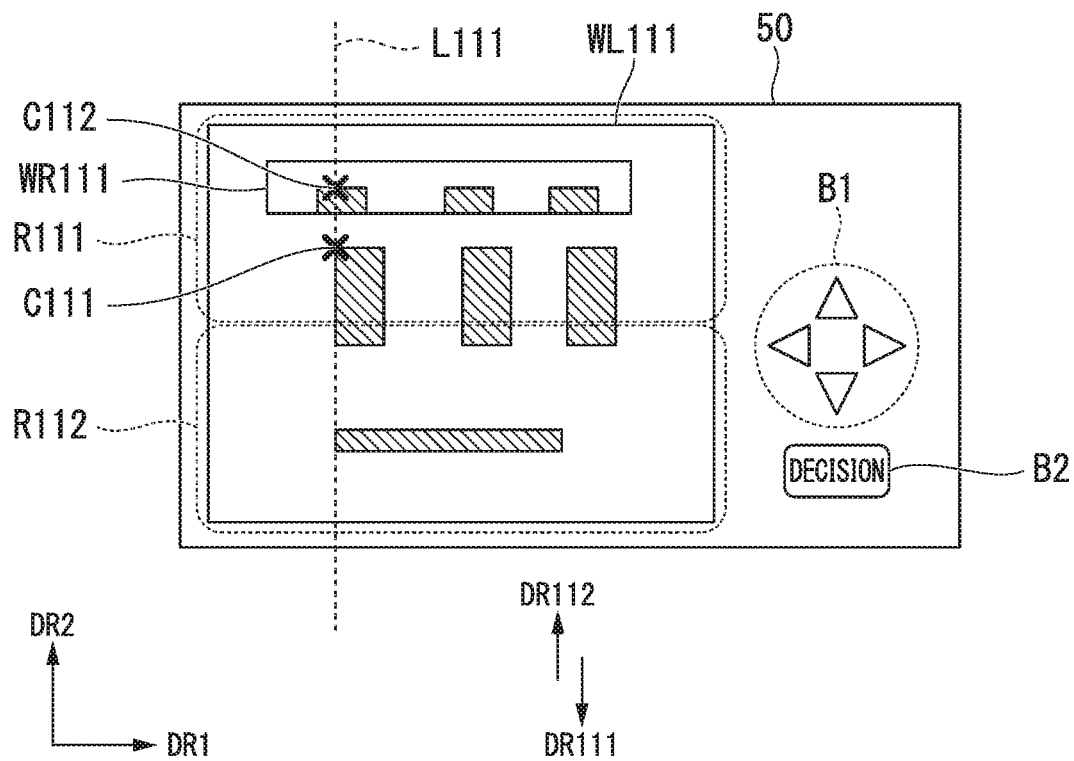
FIG. 25A is a reference diagram showing a display screen of the display unit according to a first modified example of the fourth embodiment of the present invention.
Figure 25B:
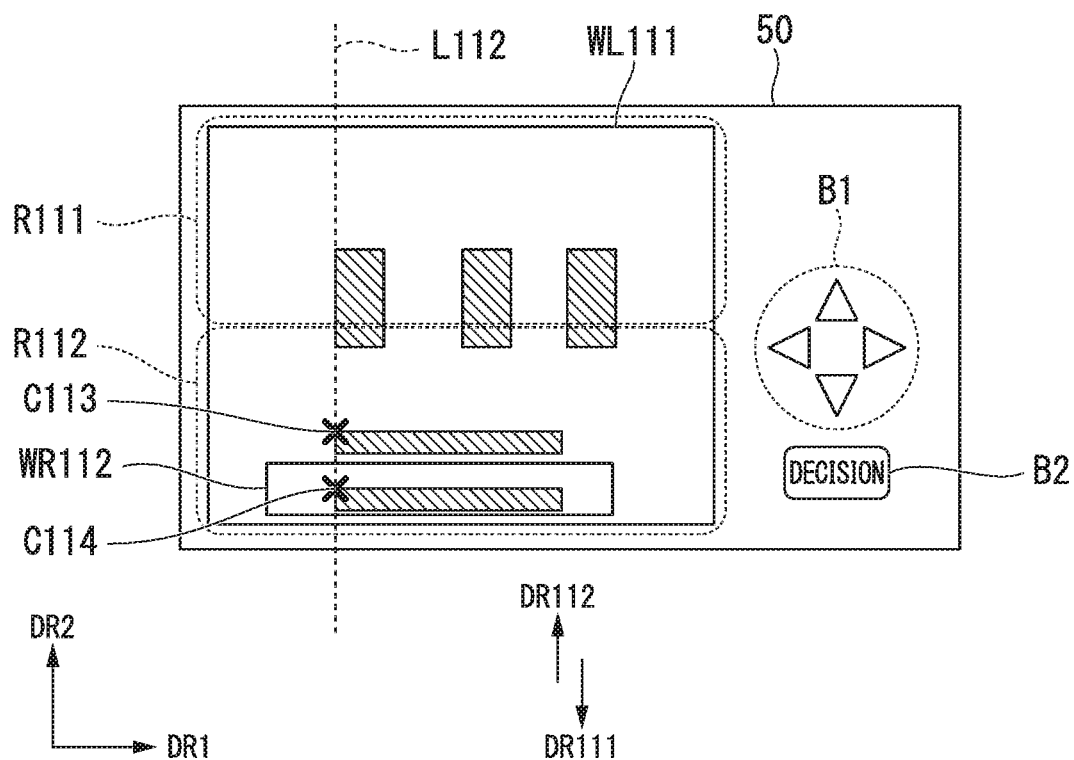
FIG. 25B is a reference diagram showing a display screen of the display unit according to the first modified example of the fourth embodiment of the present invention.

FIGS. 25A and 25B show display screens 50 of the display unit 5. The corresponding-point image display control unit 185 presets a first image region R111 and a second image region R112 in the first image displayed in a main window WL111. The first image region R111 and the second image region R112 are similar to the first image region R101 and the second image region R102 in FIGS. 24A and 24B. In FIGS. 25A and 25B, a first direction DR111 and a second direction DR112 are defined. The first direction DR111 and the second direction DR112 are similar to the first direction DR101 and the second direction DR102 in FIGS. 24A and 24B.

As shown in FIG. 25A, a first cursor C111 indicating a measurement point is located within the first image region R111. Thus, the corresponding-point image display control unit 185 causes a corresponding-point image to be displayed in the first image region R111. A sub-window WR111 including the corresponding-point image is displayed within the first image region R111. The length (width) of the sub-window WR111 in the direction DR2 orthogonal to the parallax direction DR1 is less than the length (width) of each of the first image region R111 and the second image region R112 in the direction DR2. The first cursor C111 and a second cursor C112 are disposed on a straight line L111 orthogonal to the parallax direction DR1.

As shown in FIG. 25B, a first cursor C113 indicating a measurement point is located within the second image region R112. Thus, the corresponding-point image display control unit 185 causes a corresponding-point image to be displayed in the second image region R112. A sub-window WR112 including the corresponding-point image is displayed within the second image region R112. The length (width) of the sub-window WR112 in the direction DR2 orthogonal to the parallax direction DR1 is less than the length (width) of each of the first image region R111 and the second image region R112 in the direction DR2. The first cursor C113 and a second cursor C114 are disposed on a straight line L112 orthogonal to the parallax direction DR1.

As described above, the corresponding-point image is displayed in the same image region as an image region where the measurement point is displayed. Because the corresponding-point image is easily displayed near the measurement point, the user can easily compare the first image with the corresponding-point image.

Second Modified Example of Fourth Embodiment

According to a second modified example of the fourth embodiment, the corresponding-point image display control unit 185 sets a first image region and a second image region into which a first image is bisected in the direction DR2 orthogonal to the parallax direction DR1 in the first image. A direction orthogonal to the parallax direction DR1 and directed from the first image region to the second image region is a first direction. A direction orthogonal to the parallax direction DR1 and directed from the second image region to the first image region is a second direction. The corresponding-point image display control unit 185 sets a first display region at a position on the second direction side of the first image region and sets a second display region at a position on the first direction side of the second image region on the display screen 50. When a measurement point is located within the first image region, the corresponding-point image display control unit 185 causes a corresponding-point image to be displayed in the first display region. When the measurement point is located within the second image region, the corresponding-point image display control unit 185 causes a corresponding-point image to be displayed in the second display region.

Figure 26A:
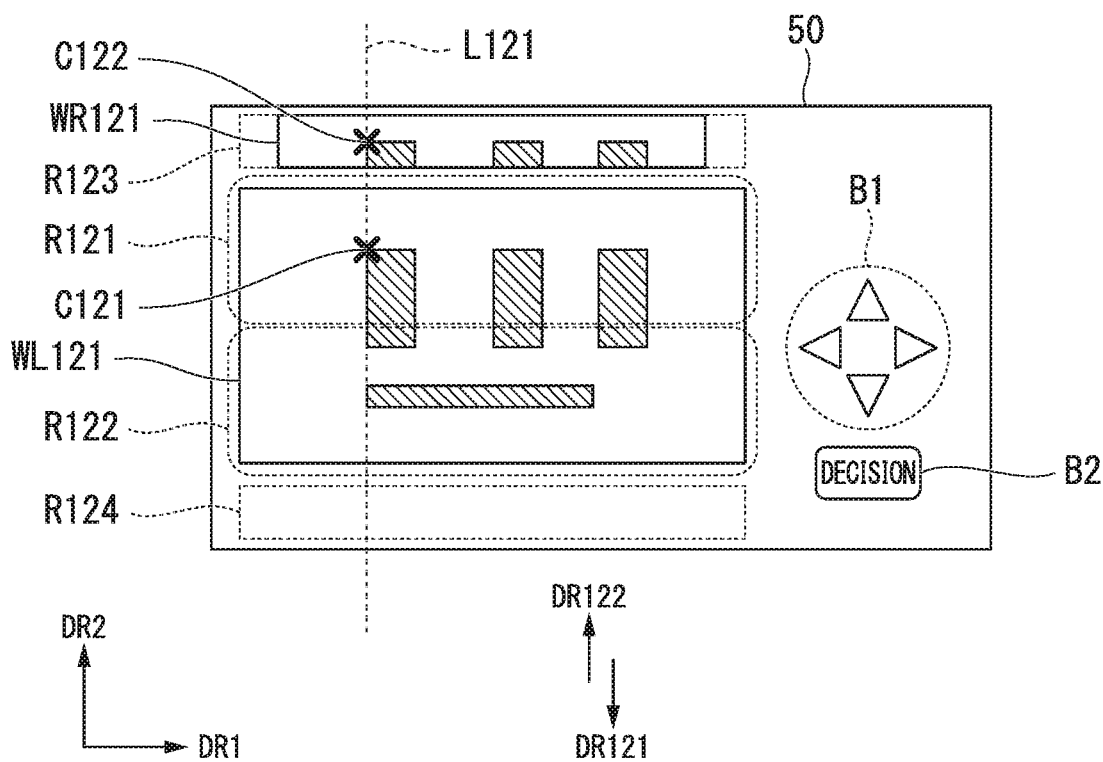
FIG. 26A is a reference diagram showing a display screen of a display unit according to a second modified example of the fourth embodiment of the present invention.
Figure 26B:
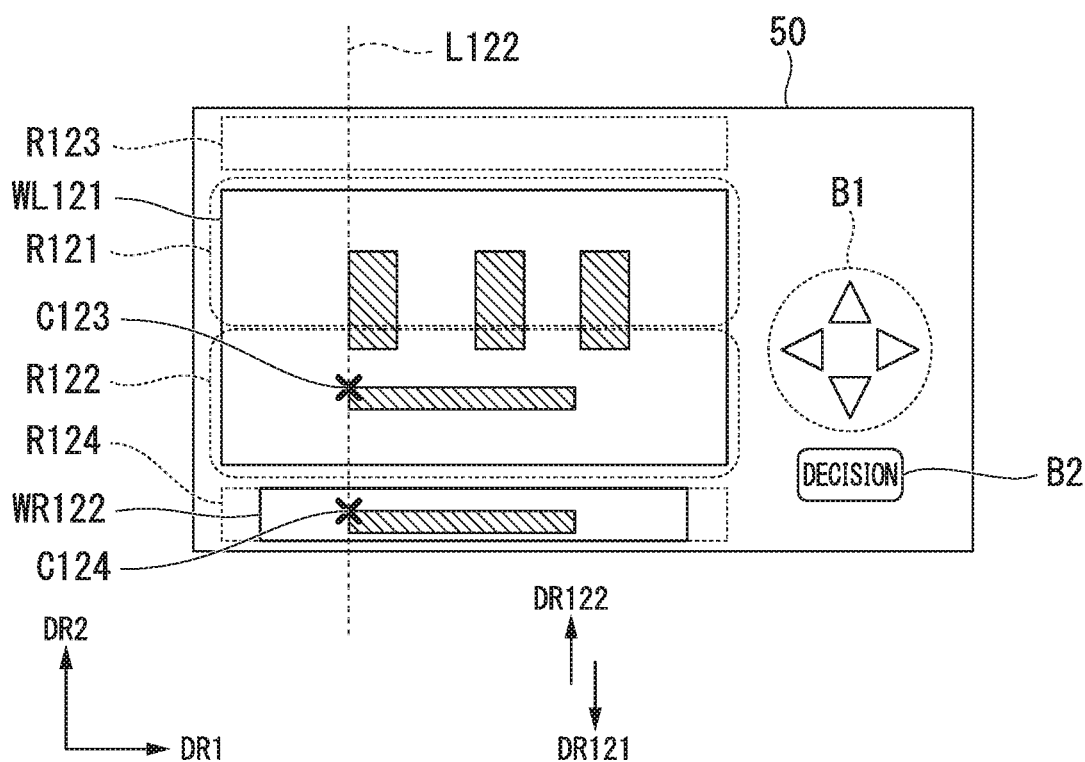
FIG. 26B is a reference diagram showing a display screen of the display unit according to the second modified example of the fourth embodiment of the present invention.

FIGS. 26A and 26B show display screens 50 of the display unit 5. The corresponding-point image display control unit 185 presets a first image region R121 and a second image region R122 in the first image displayed in a main window WL121. The first image region R121 and the second image region R122 are similar to the first image region R101 and the second image region R102 in FIGS. 24A and 24B. In FIGS. 26A and 26B, a first direction DR121 and a second direction DR122 are defined. The first direction DR121 and the second direction DR122 are similar to the first direction DR101 and the second direction DR102 in FIGS. 24A and 24B.

When there is a measurement point in the first image region R121, the corresponding-point image display control unit 185 sets a first display region R123 at a position on the second direction DR122 side of the first image region R121. The first display region R123 does not overlap the first image region R121. The first display region R123 is set between the first image region R121 and a peripheral edge portion of the display screen 50. The first display region R123 may be in contact with the first image region R121. When there is a measurement point in the second image region R122, the corresponding-point image display control unit 185 sets a second display region R124 at a position on the first direction DR121 side of the second image region R122. The second display region R124 does not overlap the second image region R122. The second display region R124 is set between the second image region R122 and the peripheral edge portion of the display screen 50. The second display region R124 may be in contact with the second image region R122.

As shown in FIG. 26A, a first cursor C121 indicating a measurement point is located within the first image region R121. Thus, the corresponding-point image display control unit 185 causes a corresponding-point image to be displayed in the first display region R123. The corresponding-point image display control unit 185 causes the corresponding-point image to be displayed in the first display region R123 closer to the first image region R121 between the first display region R123 and the second display region R124. A sub-window WR121 including the corresponding-point image is displayed within the first display region R123. The length (width) of the sub-window WR121 in the direction DR2 orthogonal to the parallax direction DR1 is the same as the length (width) of each of the first display region R123 and the second display region R124 in the direction DR2. The first cursor C121 and a second cursor C122 are disposed on a straight line L121 orthogonal to the parallax direction DR1.

As shown in FIG. 26B, a first cursor C123 indicating a measurement point is located within the second image region R122. Thus, the corresponding-point image display control unit 185 causes a corresponding-point image to be displayed in the second display region R124. The corresponding-point image display control unit 185 causes the corresponding-point image to be displayed in the second display region R124 closer to the second image region R122 between the first display region R123 and the second display region R124. A sub-window WR122 including the corresponding-point image is displayed within the second display region R124. The length (width) of the sub-window WR122 in the direction DR2 orthogonal to the parallax direction DR1 is the same as the length (width) of each of the first display region R123 and the second display region R124 in the direction DR2. The first cursor C123 and a second cursor C124 are disposed on a straight line L122 orthogonal to the parallax direction DR1.

Fifth Embodiment

In a fifth embodiment of the present invention, a measurement point image of the vicinity of a measurement point is generated from a first image. In the fifth embodiment, a corresponding-point image is displayed so that a straight line passing through the measurement point in the measurement point image and a corresponding point in the corresponding-point image is orthogonal to a parallax direction DR1.

Figure 27:
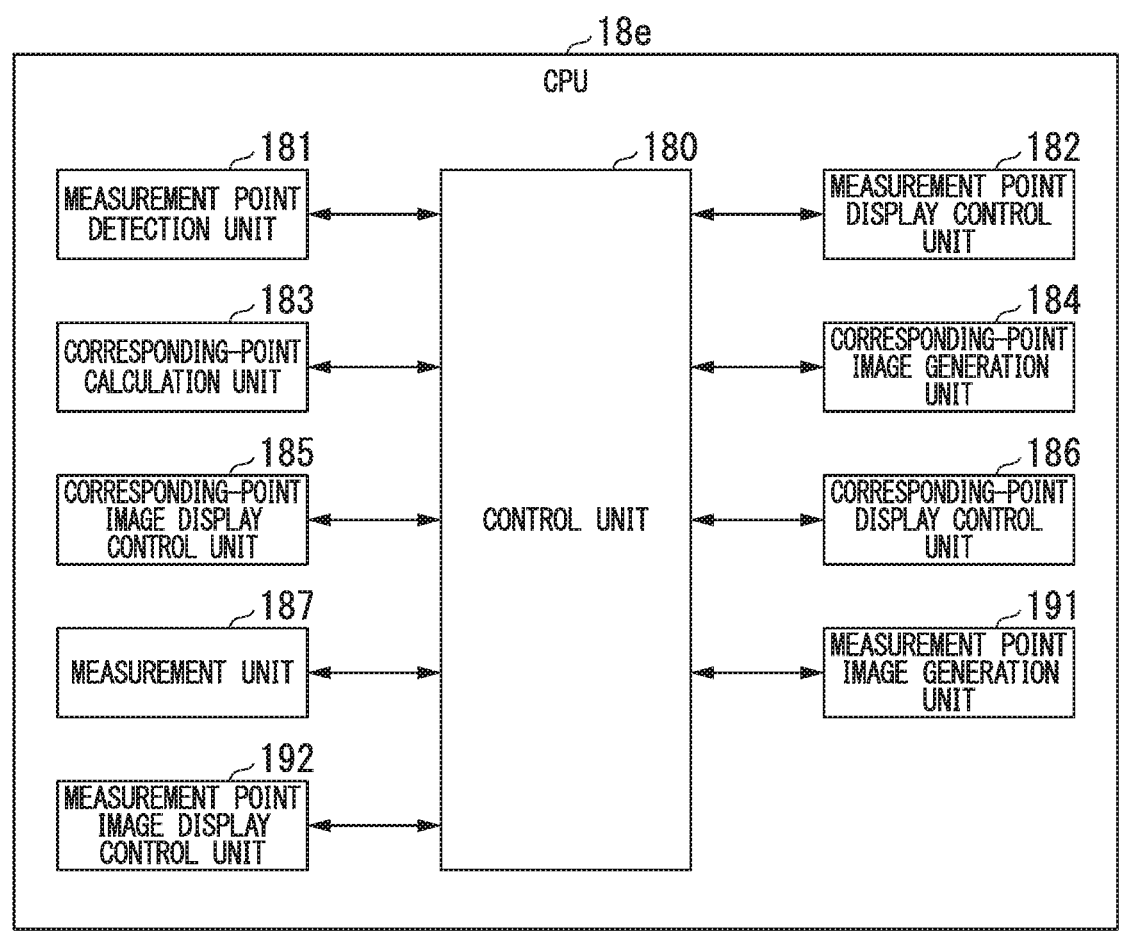
FIG. 27 is a block diagram showing a functional configuration of a CPU according to a fifth embodiment of the present invention.

In the fifth embodiment, the CPU 18a is changed to a CPU 18e shown in FIG. 27. FIG. 27 shows a functional configuration of the CPU 18e. The configuration shown in FIG. 27 will be described in terms of differences from the configuration shown in FIG. 5.

In addition to the configuration shown in FIG. 5, the CPU 18e includes a measurement point image generation unit 191 and a measurement point image display control unit 192. The measurement point image generation unit 191 generates a measurement point image that includes a measurement point and a region in the vicinity of the measurement point in a first image and is constituted of a part of the first image. The measurement point image display control unit 192 causes the measurement point image to be displayed on a display screen 50. A corresponding-point image display control unit 185 causes the corresponding-point image to be displayed on the display screen 50 so that a straight line passing through the measurement point in the measurement point image and a corresponding point in a corresponding-point image is orthogonal to the parallax direction DR1.

Regarding points other than the above, a configuration shown in FIG. 27 is similar to the configuration shown in FIG. 5.

Figure 28:
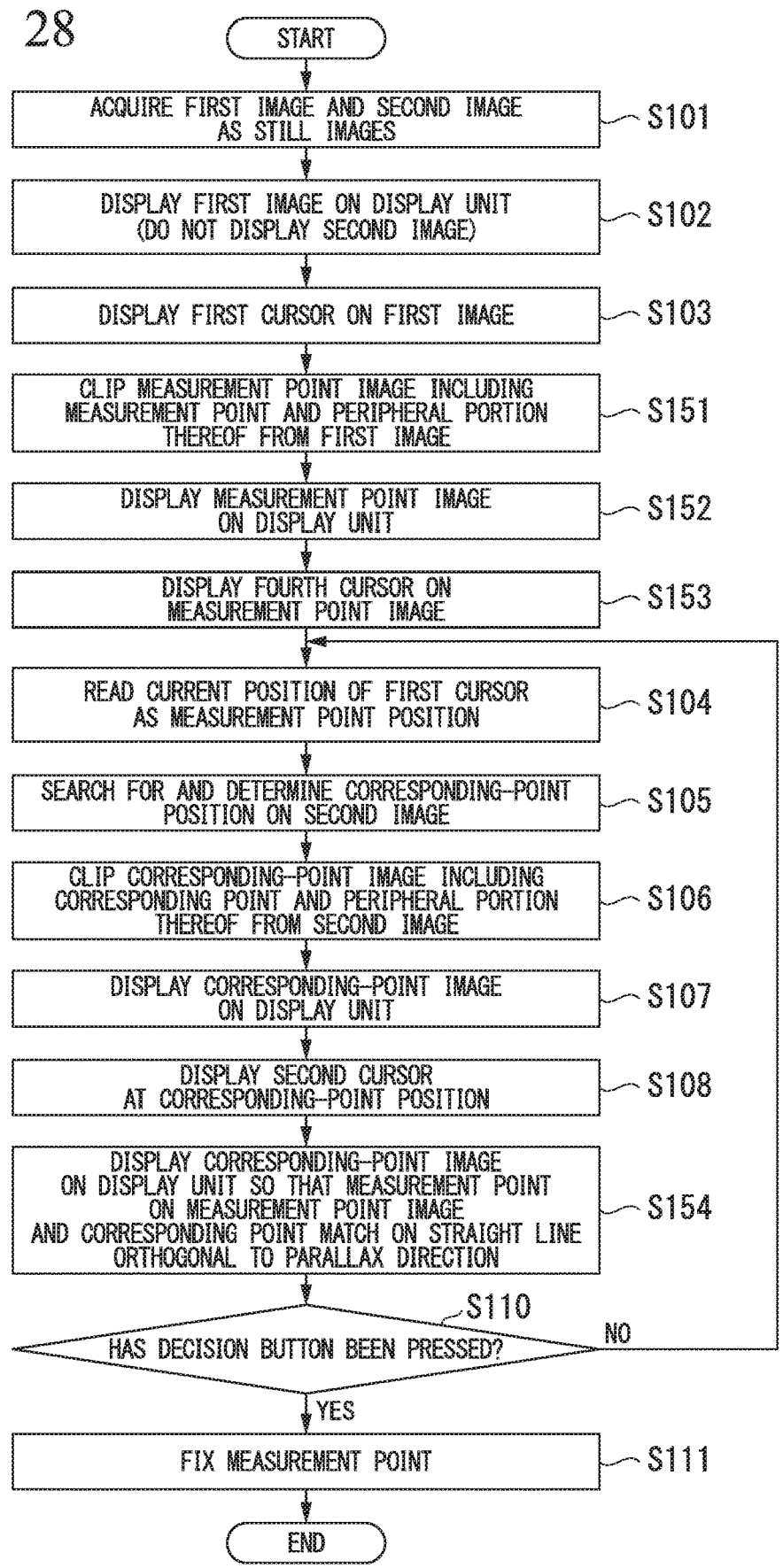
FIG. 28 is a flowchart showing a procedure of an operation of an endoscopic measurement device according to the fifth embodiment of the present invention.
Figure 29A:
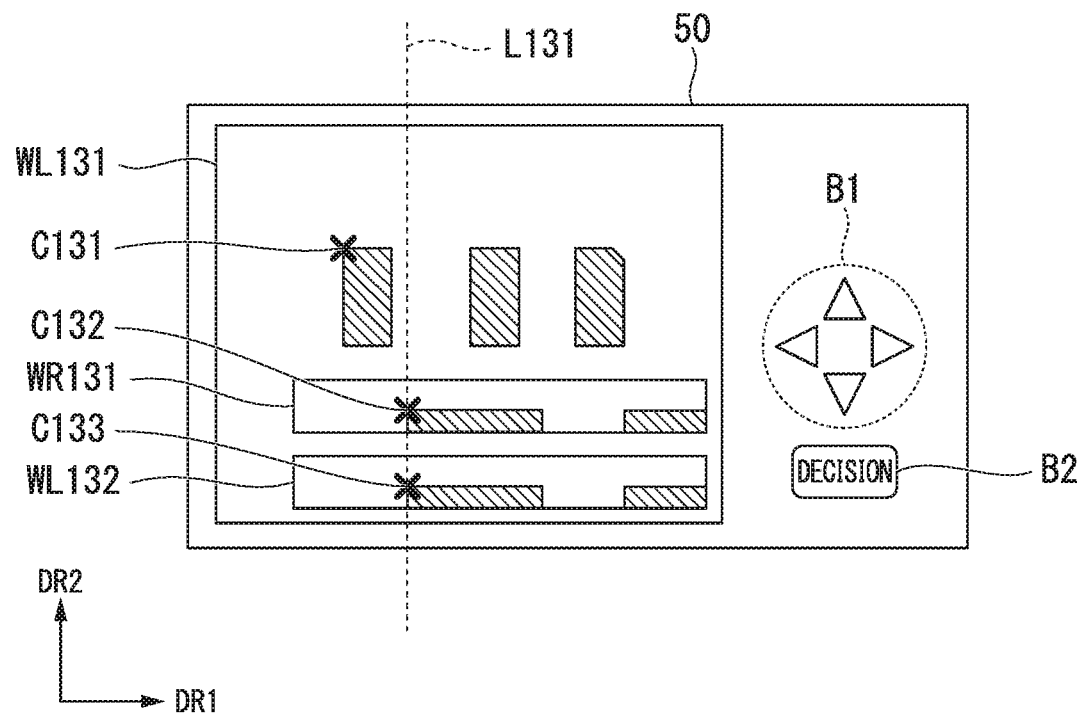
FIG. 29A is a reference diagram showing a display screen of a display unit according to the fifth embodiment of the present invention.
Figure 29B:
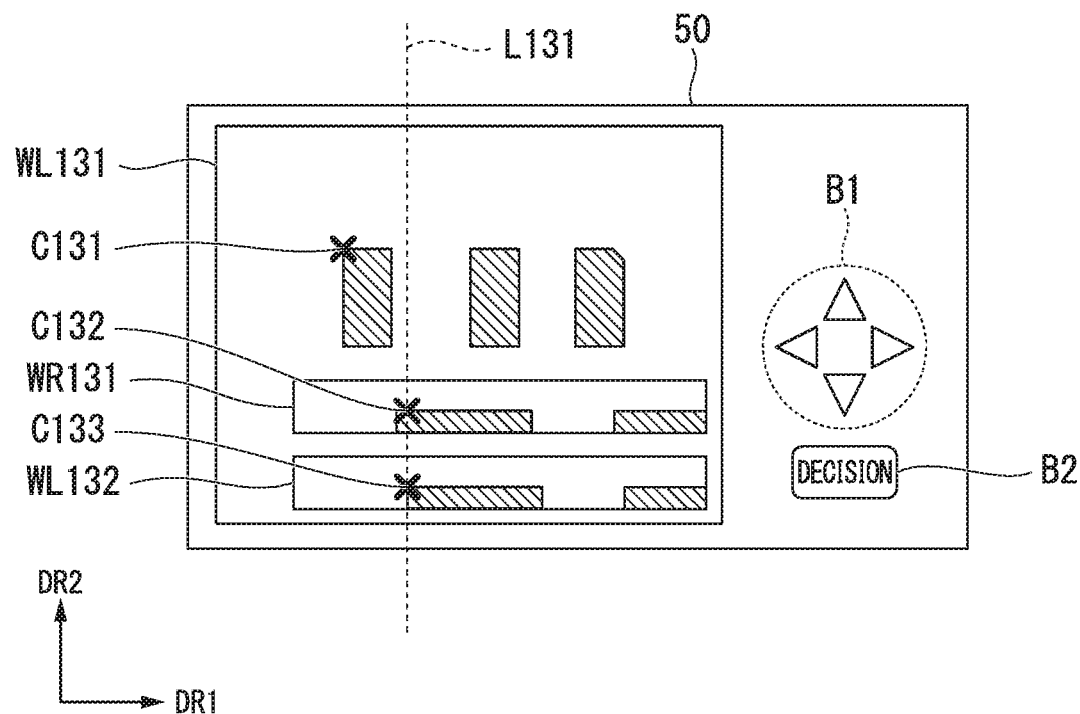
FIG. 29B is a reference diagram showing a display screen of the display unit according to the fifth embodiment of the present invention.

A process according to the fifth embodiment will be described with reference to FIGS. 28, 29A, and 29B. FIG. 28 shows a process in the measurement mode. FIGS. 29A and 29B show display screens 50 of a display unit 5. As shown in FIGS. 29A and 29B, a first image is displayed in a main window WL131 and a first cursor C131 indicating a measurement point is displayed in the main window WL131.

The process shown in FIG. 28 will be described in terms of differences from the process shown in FIG. 7. After step S103, the measurement point image generation unit 191 generates a measurement point image that includes a measurement point and a region in the vicinity of the measurement point in a first image and is constituted of a part of the first image. At this time, the measurement point image generation unit 191 generates a measurement point image of which a length in the parallax direction DR1 is greater than a length in a direction DR2 orthogonal to the parallax direction DR1. That is, the measurement point image generation unit 191 generates a corresponding-point image elongated in the parallax direction DR1 (step S151).

After step S151, the measurement point image display control unit 192 generates an image signal of a sub-window WL132 including the measurement point image. The measurement point image display control unit 192 outputs the generated image signal to a video signal processing circuit 12. The video signal processing circuit 12 synthesizes a video signal output from a CCU 9 with the image signal output from the CPU 18e. Thereby, the sub-window WL132 including the measurement point image is displayed. The video signal processing circuit 12 outputs the synthesized video signal to the display unit 5. The display unit 5 displays the sub-window WL132 including the measurement point image (step S152). In the measurement point image included in the sub-window WL132, a structure of an object appears.

As shown in FIGS. 29A and 29B, the sub-window WL132 is superimposed on the main window WL131. In step S152, the measurement point image display control unit 192 causes the measurement point image to be displayed on the first image. At this time, the measurement point image display control unit 192 causes the measurement point image to be displayed so that all or a part of the measurement point image overlaps the first image. In FIGS. 29A and 29B, the entire measurement point image in the sub-window WL132 overlaps the first image within the main window WL131. In the main window WL131, the first image of the region where the main window WL131 and the sub-window WL132 overlap each other cannot be visually recognized. In step S152, the measurement point image display control unit 192 sets a display region (the sub-window WL132) of the measurement point image in the first image and causes the measurement point image to be displayed within the sub-window WL132.

In step S152, the measurement point image display control unit 192 causes the measurement point image to be displayed so that the parallax direction in the measurement point image is parallel to the parallax direction DR1 in the first image. That is, the measurement point image display control unit 192 causes the measurement point image to be displayed so that the measurement point image is not inclined with respect to the first image.

In step S152, the measurement point image display control unit 192 causes the measurement point image to be displayed so that a position of the measurement point on the measurement point image in the parallax direction DR1 is different from a position of the measurement point on the first image. That is, the measurement point image display control unit 192 causes the measurement point image to be displayed so that the measurement point in the measurement point image is shifted in the parallax direction DR1 with respect to the measurement point in the first image. The measurement point image display control unit 192 may cause the measurement point image to be displayed so that the position of the measurement point on the measurement point image in the parallax direction DR1 matches the position of the measurement point on the first image. In this case, the measurement point in the first image, the measurement point in the measurement point image, and the corresponding point in the corresponding-point image are disposed on a straight line orthogonal to the parallax direction DR1.

In step S152, the measurement point image display control unit 192 causes the measurement point image to be displayed so that a position of the measurement point on the measurement point image in the direction DR2 orthogonal to the parallax direction DR1 is different from a position of the measurement point on the first image. That is, the measurement point image display control unit 192 causes the measurement point image to be displayed so that the measurement point in the measurement point image is shifted in the direction DR2 with respect to the measurement point in the first image. The measurement point image display control unit 192 may cause the measurement point image to be displayed so that a position of the measurement point on the measurement point image in the direction DR2 is the same as a position of the measurement point on the first image. In this case, the measurement point in the first image and the measurement point in the measurement point image are disposed on a straight line parallel to the parallax direction DR1.

In step S152, the measurement point image display control unit 192 causes the measurement point image to be displayed so that the measurement point in the measurement point image is separated from the measurement point in the first image. That is, the measurement point image display control unit 192 causes the measurement point image to be displayed so that a position of the measurement point in the measurement point image is different from a position of the measurement point in the first image. The measurement point image display control unit 192 may cause the measurement point image to be displayed so that a position of the measurement point in the measurement point image matches a position of the measurement point in the first image.

In step S152, the measurement point image display control unit 192 causes the measurement point image to be displayed so that the measurement point image is separated from the measurement point in the first image. That is, the measurement point image display control unit 192 causes the measurement point image to be displayed so that the measurement point image does not overlap the measurement point in the first image. The measurement point image display control unit 192 may cause the measurement point image to be displayed so that the measurement point image overlaps the measurement point in the first image.

In step S152, the measurement point image display control unit 192 causes the measurement point image to be displayed at display magnification higher than that of the first image. Thereby, the sub-window WL132 can be used as a zoom window for displaying an enlarged image. The measurement point image display control unit 192 may cause the measurement point image to be displayed at the same display magnification as that of the first image. The sub-window WL132 may be used for purposes other than that of the zoom window. For example, a reduced image, a depth image (a depth map), or a reliability map may be displayed in the sub-window WL132.

After step S152, a fourth cursor C133 is displayed so that the user can easily check the position of the measurement point in the measurement point image. The measurement point display control unit 182 causes the fourth cursor C133 indicating a measurement point in the measurement point image to be displayed on the display screen 50. At this time, the measurement point display control unit 182 causes the fourth cursor C133 to be displayed on the measurement point image (step S153). After step S153, the processing of step S104 is performed. A position of the fourth cursor C133 is the same as a position of the measurement point in the measurement point image. The fourth cursor C133 indicates the same position as a position on the object indicated by the first cursor C131. The fourth cursor C133 moves in conjunction with the movement of the first cursor C131. A process related to the movement of the fourth cursor C133 is not shown in FIG. 28.

As shown in FIGS. 29A and 29B, the fourth cursor C133 is separated from the first cursor C131. That is, the measurement point in the measurement point image is separated from the measurement point in the first image. Because the measurement point image is displayed so that the measurement point image is separated from the measurement point in the first image, the sub-window WR132 does not overlap the first cursor C131.

After step S108, the corresponding-point image display control unit 185 adjusts a position of the corresponding-point image within the sub-window WR131. Specifically, the corresponding-point image display control unit 185 causes the corresponding-point image to be displayed so that a measurement point in the measurement point image and a corresponding point in the corresponding-point image are disposed on a straight line L131. The straight line L131 passes through the fourth cursor C133 and a second cursor C132. That is, the straight line L131 passes through the measurement point in the measurement point image and the corresponding point in the corresponding-point image. The straight line L131 is orthogonal to the parallax direction DR1 in the first image and the second image. Therefore, the corresponding-point image display control unit 185 adjusts the position of the corresponding-point image on the display screen 50 so that the straight line L131 passing through the measurement point in the measurement point image and the corresponding point in the corresponding-point image is orthogonal to the parallax direction DR1 (step S154). At this time, the straight line L131 is not displayed on the display screen 50.

In step S154, the measurement point display control unit 182 adjusts the position of the fourth cursor C133 and the corresponding-point display control unit 186 adjusts the position of the second cursor C132. That is, the measurement point display control unit 182 causes the fourth cursor C133 to be displayed on the straight line L131 on the display screen 50. The corresponding-point display control unit 186 causes the second cursor C132 to be displayed on the straight line L131 on the display screen 50. After step S154, the processing of step S110 is performed.

In step S107, the corresponding-point image display control unit 185 may cause the corresponding-point image to be displayed at the same display magnification as that of the measurement point image. Thereby, the user can easily check whether or not erroneous matching correspondence has occurred.

Regarding points other than the above, the process shown in FIG. 28 is similar to the process shown in FIG. 7.

FIG. 29A shows a display screen 50 of the display unit 5 when no erroneous matching correspondence has occurred. The positions indicated by the fourth cursor C133 and the second cursor C132 match in the object. That is, positions of the measurement point and the corresponding point on the object match. After a position of the corresponding-point image is adjusted so that the straight line L131 passing through the measurement point in the measurement point image and the corresponding point in the corresponding-point image is orthogonal to the parallax direction DR1, a position of a structure around the measurement point within the measurement point image in the parallax direction DR1 is the same as a position of a structure around the corresponding point within the corresponding-point image. Thus, the user can determine that no erroneous matching correspondence has occurred.

FIG. 29B shows a display screen 50 of the display unit 5 when erroneous matching correspondence has occurred. Positions indicated by the fourth cursor C133 and the second cursor C132 do not match in the object. That is, the positions of the measurement point on the object and the corresponding point do not match. Specifically, the corresponding point in the corresponding-point image is shifted to a right side of the position of the measurement point in the object of the measurement point image. After the position of the corresponding-point image is adjusted so that the straight line L131 passing through the measurement point in the measurement point image and the corresponding point in the corresponding-point image is orthogonal to the parallax direction DR1, a position of a structure around the corresponding point within the corresponding-point image is shifted to a left side of a position of a structure around the measurement point within the measurement point image. Thus, the user can determine that erroneous matching correspondence has occurred.

The user can check a state of the entire object using the main window WL131 for displaying the first image. At the same time, the user can check a fine texture (pattern), a color, and an edge position of the object using the sub-window WL132 in which the measurement point image is enlarged and displayed. Thus, the user can easily check whether or not erroneous matching correspondence has occurred.

(Supplement)

When a corresponding-point image is displayed on a first image so that a measurement point and a corresponding point overlap each other, the corresponding-point image may be displayed to cover the first image from above. In other words, the first image of a region where the first image and the corresponding-point image overlap each other need not be visibly recognized.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A measurement processing device comprising:
an image sensor configured to image an object and generate an imaging signal; and
a processor comprising hardware, wherein the processor is configured to:
acquire a first image and a second image mutually having parallax in a predetermined parallax direction on the basis of the imaging signal;
control a display screen to display the first image;
control the display screen to display a measurement point indicating a measurement position designated by a user on the first image;
calculate a corresponding point on the second image corresponding to the measurement point on the first image;
generate a corresponding-point image that includes the corresponding point and a region in the vicinity of the corresponding point in the second image and is constituted of all or a part of the second image; and
control the display screen to display the corresponding-point image so that a straight line passing through the measurement point and the corresponding point is orthogonal to the parallax direction,
wherein the processor is configured to generate the corresponding-point image of which a length in the parallax direction is greater than a length in a direction orthogonal to the parallax direction.

2. The measurement processing device according to claim 1,
wherein the processor is configured to:
generate a second corresponding-point image of which the length in the parallax direction is less than the length in the direction orthogonal to the parallax direction, the second corresponding-point image including the corresponding point and a region in the vicinity of the corresponding point in the second image and being constituted of all or a part of the second image; and
control the display screen to display the second corresponding-point image so that the first image and the second corresponding-point image are arranged in the parallax direction.

3. The measurement processing device according to claim 2,
wherein the processor is configured to control the display screen to display an auxiliary line parallel to the parallax direction and passing through the measurement point on the first image and the second corresponding-point image.

4. A measurement processing device comprising:
an image sensor configured to image an object and generate an imaging signal; and
a processor comprising hardware, wherein the processor is configured to:
acquire a first image and a second image mutually having parallax in a predetermined parallax direction on the basis of the imaging signal;
control a display screen to display the first image;
control the display screen to display a measurement point indicating a measurement position designated by a user on the first image;
calculate a corresponding point on the second image corresponding to the measurement point on the first image;
generate a corresponding-point image that includes the corresponding point and a region in the vicinity of the corresponding point in the second image and is constituted of all or a part of the second image; and
control the display screen to display the corresponding-point image so that a straight line passing through the measurement point and the corresponding point is orthogonal to the parallax direction,
wherein the processor is configured to control the display screen to display the corresponding-point image so that the corresponding point is separated from the measurement point, and
wherein the processor is configured to control the display screen to display one or more auxiliary lines orthogonal to the parallax direction on the first image and the corresponding-point image on the display screen.

5. The measurement processing device according to claim 4,
wherein the processor is configured to control the display screen to display the auxiliary line so that the auxiliary line passes through the measurement point.

6. The measurement processing device according to claim 4,
wherein the processor is configured to:
calculate a first feature point other than the measurement point in the object of the first image; and
control the display screen to display the auxiliary line so that the auxiliary line passes through the first feature point.

7. The measurement processing device according to claim 4,
wherein the processor is configured to:
calculate a second feature point other than the corresponding point in the object of the first image in the object of the corresponding-point image; and
control the display screen to display the auxiliary line so that the auxiliary line passes through the second feature point.

8. A measurement processing device comprising:
an image sensor configured to image an object and generate an imaging signal; and
a processor comprising hardware, wherein the processor is configured to:
acquire a first image and a second image mutually having parallax in a predetermined parallax direction on the basis of the imaging signal;
control a display screen to display the first image;
control the display screen to display a measurement point indicating a measurement position designated by a user on the first image;
calculate a corresponding point on the second image corresponding to the measurement point on the first image;
generate a corresponding-point image that includes the corresponding point and a region in the vicinity of the corresponding point in the second image and is constituted of all or a part of the second image; and
control the display screen to display the corresponding-point image so that a straight line passing through the measurement point and the corresponding point is orthogonal to the parallax direction,
wherein the processor is configured to control the display screen to display the corresponding-point image so that the corresponding point is separated from the measurement point, and
wherein the processor is configured to:
calculate a feature point other than the measurement point in the object of the first image;

calculate a corresponding feature point on the second image corresponding to the feature point on the first image; and control the display screen to display an auxiliary line passing through the feature point and the corresponding feature point.

9. A measurement processing device comprising:

an image sensor configured to image an object and generate an imaging signal; and a processor comprising hardware, wherein the processor is configured to:

acquire a first image and a second image mutually having parallax in a predetermined parallax direction on the basis of the imaging signal;

control a display screen to display the first image;

control the display screen to display a measurement point indicating a measurement position designated by a user on the first image;

calculate a corresponding point on the second image corresponding to the measurement point on the first image;

generate a corresponding-point image that includes the corresponding point and a region in the vicinity of the corresponding point in the second image and is constituted of all or a part of the second image; and control the display screen to display the corresponding-point image so that a straight line passing through the measurement point and the corresponding point is orthogonal to the parallax direction, wherein the processor is configured to control the display screen to display the corresponding-point image so that the corresponding point is separated from the measurement point, and wherein the processor is configured to control a display position of the corresponding-point image in accordance with a position of the measurement point.

10. The measurement processing device according to claim 9, wherein the processor is configured to:

set a plurality of image regions arranged in a direction orthogonal to the parallax direction in the first image, wherein the plurality of image regions include a first image region and a second image region, wherein a direction orthogonal to the parallax direction and directed from the first image region to the second image region is defined as a first direction, and wherein a direction orthogonal to the parallax direction and directed from the second image region to the first image region is defined as a second direction;

control the display screen to display the corresponding-point image at a position on the first direction side of the measurement point when the measurement point is located within the first image region; and control the display screen to display the corresponding-point image at a position on the second direction side of the measurement point when the measurement point is located within the second image region.

11. The measurement processing device according to claim 10, wherein the processor is configured to control the display screen to display the corresponding-point image on the first image.

12. The measurement processing device according to claim 9, wherein the processor is configured to:

set a plurality of image regions arranged in a direction orthogonal to the parallax direction in the first image, wherein the plurality of image regions include a first image region and a second image region;

control the display screen to display the corresponding-point image in the first image region when the measurement point is located within the first image region; and control the display screen to display the corresponding-point image in the second image region when the measurement point is located within the second image region.

13. The measurement processing device according to claim 9, wherein the processor is configured to:

set a first image region and a second image region obtained by bisecting the first image in a direction orthogonal to the parallax direction in the first image, wherein a direction orthogonal to the parallax direction and directed from the first image region to the second image region is defined as a first direction, and wherein a direction orthogonal to the parallax direction and directed from the second image region to the first image region is defined as a second direction, set a first display region at a position on the second direction side of the first image region and set a second display region at a position on the first direction side of the second image region on the display screen;

control the display screen to display the corresponding-point image in the first image region when the measurement point is located within the first image region; and control the display screen to display the corresponding-point image in the second image region when the measurement point is located within the second image region.

14. A measurement processing device comprising:

an image sensor configured to image an object and generate an imaging signal; and a processor comprising hardware, wherein the processor is configured to:

acquire a first image and a second image mutually having parallax in a predetermined parallax direction on the basis of the imaging signal;

control a display screen to display the first image;

control the display screen to display a measurement point indicating a measurement position designated by a user on the first image;

calculate a corresponding point on the second image corresponding to the measurement point on the first image;

generate a corresponding-point image that includes the corresponding point and a region in the vicinity of the corresponding point in the second image and is constituted of all or a part of the second image; and control the display screen to display the corresponding-point image so that a straight line passing through the measurement point and the corresponding point is orthogonal to the parallax direction, wherein the processor is configured to:
- generate a measurement point image that includes the measurement point and a region in the vicinity of the measurement point in the first image and is constituted of a part of the first image;
- control the display screen to display the measurement point image; and
- control the display screen to display the corresponding-point image so that a straight line passing through the measurement point in the measurement point image and the corresponding point in the corresponding-point image is orthogonal to the parallax direction on the display screen.

15. The measurement processing device according to claim 14,
wherein the processor is configured to control the display screen to display the measurement point image at display magnification higher than that of the first image.

16. The measurement processing device according to claim 15,
wherein the processor is configured to cause the display screen to display the corresponding-point image at the same display magnification as that of the measurement point image.

17. A measurement processing device comprising:
an image sensor configured to image an object and generate an imaging signal; and
a processor comprising hardware, wherein the processor is configured to:
- acquire a first image and a second image mutually having parallax in a predetermined parallax direction on the basis of the imaging signal;
- control a display screen to display the first image;
- control the display screen to display a measurement point indicating a measurement position designated by a user on the first image;
- calculate a corresponding point on the second image corresponding to the measurement point on the first image;
- generate a corresponding-point image that includes the corresponding point and a region in the vicinity of the corresponding point in the second image and is constituted of all or a part of the second image; and
- control the display screen to display the corresponding-point image so that a straight line passing through the measurement point and the corresponding point is orthogonal to the parallax direction, wherein the processor is configured to:
- control the display screen to display the corresponding point on the corresponding-point image;
- control the display screen to display a first cursor indicating the measurement point on the straight line; and
- control the display screen to display a second cursor indicating the corresponding point to be displayed on the straight line.

18. A measurement processing device comprising:
an image sensor configured to image an object and generate an imaging signal; and
a processor comprising hardware, wherein the processor is configured to:
- acquire a first image and a second image mutually having parallax in a predetermined parallax direction on the basis of the imaging signal;
- control a display screen to display the first image;
- control the display screen to display a measurement point indicating a measurement position designated by a user on the first image;
- calculate a corresponding point on the second image corresponding to the measurement point on the first image;
- generate a corresponding-point image that includes the corresponding point and a region in the vicinity of the corresponding point in the second image and is constituted of all or a part of the second image; and
- control the display screen to display the corresponding-point image so that a straight line passing through the measurement point and the corresponding point is orthogonal to the parallax direction, wherein the processor is configured to control the display screen to display the corresponding-point image at the same display magnification as that of the first image.

* * * * *